United States Patent
Karsdal et al.

(10) Patent No.: US 10,350,272 B2
(45) Date of Patent: *Jul. 16, 2019

(54) CALCITONIN ANALOGUES FOR TREATING DISEASES AND DISORDERS

(71) Applicant: KeyBioscience AG, Stans (CH)

(72) Inventors: Morten Karsdal, Kobenhavn Ø (DK); Kim Henriksen, Hillerød (DK); Kim Vietz Andreassen, Ballerup (DK); Sofie Gydesen, Valby (DK); Sara Toftegaard Hjuler, Veksø Sj (DK)

(73) Assignee: KeyBioscience AG, Stans (CH)

( * ) Notice: Subject to any disclaimer, the term of this patent is extended or adjusted under 35 U.S.C. 154(b) by 0 days.

This patent is subject to a terminal disclaimer.

(21) Appl. No.: 15/542,191

(22) PCT Filed: Jan. 7, 2016

(86) PCT No.: PCT/EP2016/050186
§ 371 (c)(1),
(2) Date: Jul. 7, 2017

(87) PCT Pub. No.: WO2016/110525
PCT Pub. Date: Jul. 14, 2016

(65) Prior Publication Data
US 2018/0264085 A1    Sep. 20, 2018

(30) Foreign Application Priority Data

Jan. 8, 2015    (GB) .................................. 1500263.7

(51) Int. Cl.
*A61K 38/23*    (2006.01)
*A61P 1/16*    (2006.01)
*A61P 3/06*    (2006.01)

(52) U.S. Cl.
CPC .................................. *A61K 38/23* (2013.01)

(58) Field of Classification Search
None
See application file for complete search history.

(56) References Cited

U.S. PATENT DOCUMENTS

| | | | |
|---|---|---|---|
| 4,708,934 A | 11/1987 | Gilligan et al. | |
| 5,102,666 A | 4/1992 | Acharya | |
| 5,438,040 A | 8/1995 | Ekwuribe | |
| 5,773,647 A | 6/1998 | Leone-Bay et al. | |
| 5,866,536 A | 2/1999 | Leone-Bay et al. | |
| 5,912,014 A | 6/1999 | Stern et al. | |
| 6,086,918 A | 7/2000 | Stern et al. | |
| 6,673,574 B2 | 1/2004 | Stern et al. | |
| 7,189,414 B2 | 3/2007 | Rubinstein et al. | |
| 7,268,214 B2 | 9/2007 | O'Mahony et al. | |
| 7,316,819 B2 | 1/2008 | Crotts et al. | |
| 7,445,911 B2 | 11/2008 | Consalvo et al. | |
| 8,093,207 B2 | 1/2012 | Stern | |
| 2002/0115592 A1 | 8/2002 | New et al. | |
| 2003/0069170 A1 | 4/2003 | Soltero et al. | |
| 2006/0292672 A1 | 12/2006 | Miller et al. | |
| 2007/0238707 A1 | 10/2007 | Leonard | |
| 2008/0200563 A1 | 8/2008 | Hoffer | |
| 2009/0074824 A1 | 3/2009 | Vila Pena | |
| 2009/0087479 A1 | 4/2009 | Lau et al. | |
| 2009/0317462 A1 | 12/2009 | Stern et al. | |
| 2013/0183385 A1* | 7/2013 | Mehta .................. | C07K 14/585 424/490 |

FOREIGN PATENT DOCUMENTS

| | | |
|---|---|---|
| EP | 0308067 A2 | 3/1989 |
| EP | 0382403 A2 | 8/1990 |
| WO | 00/59863 A1 | 10/2000 |
| WO | 02/28436 A1 | 4/2002 |
| WO | 2004/084870 A1 | 10/2004 |
| WO | 2004/091584 A1 | 10/2004 |
| WO | 2005/014031 A1 | 2/2005 |
| WO | 2005/094785 A2 | 10/2005 |
| WO | 2007/029238 A2 | 3/2007 |
| WO | 2013/067357 A1 | 5/2013 |

OTHER PUBLICATIONS

Ray et al, Biotechnology, Production of Recombinant Salmon Calcitonin by In Vitro Amidation of an *Escherichia coli* Produced Precursor, Peptide, (1993), 11: 64-70.
Ray et al, Protein Expression and Purification, Production of salmon calcitonin by direct expression of a glycine-extended precursor in *Escherichia coli*, (2002), 26:249-259.
Mehta, N. M., Oral Delivery and Recombinant Production of Peptide Hormones, Part II: Recombinant Production of Therapeutic Peptides. Biopharm. International, (2004), July, pp. 44-46.
Mansoor et al, Oral Delivery of Mono-PEGylated sCT (Lys18) in Rats: Regional Difference in Stability and Hypocalcemic Effect. Pharmaceutical Development and Technology, (2005), 10:389-396.
Prego et al, Chitosan-PEG nanocapsules as new carriers for oral peptide delivery Effect of chitosan pegylation degree. Journal of Controlled Release, (2006), 111:299-308.
Garcia-Fuentes et al., A comparative study of the potential of solid triglyceride nanostructures coated with chitosan or poly(ethylene glycol) as carriers for oral calcitonin delivery. European Journal of Pharmaceutical Sciences, (2005), 25:133-143.
Garcia-Fuentes et al, New surface-modified lipid nanoparticles as delivery vehicles for salmon calcitonin. International Journal of Pharmaceutics, (2005), 296:122-132.
Guggi et al, Systemic peptide delivery via the stomach: in vivo evaluation of an oral dosage form for salmon calcitonin. Journal of Controlled Release, (2003), 92:125-135.
Guggi et al, In Vivo Evaluation of an Oral Salmon Calcitonin-Delivery System Based on a Thiolated Chitosan Carrier Matrix. Pharmaceutical Research, (2003), 20 (12): 1989-1994.
Dogru et al, Oral multiple w/o/w emulsion formulation of a peptide salmon calcitonin: in vitro-in vivo evaluation. Journal of Clinical Pharmacy and Therapeutics, (2000), 25:435-443.

(Continued)

*Primary Examiner* — Julie Ha
*Assistant Examiner* — Kristina M Hellman
(74) *Attorney, Agent, or Firm* — Benjamin Aaron Adler

(57) ABSTRACT

Calcitonin analogues as a medicament for producing a decrease in liver triglycerides or for reducing fat accumulation in the liver of a subject are provided.

5 Claims, 13 Drawing Sheets

Specification includes a Sequence Listing.

(56) References Cited

OTHER PUBLICATIONS

Sinko et al, Biopharmaceutical Approaches for Developing and Assessing Oral Peptide Delivery Strategies and Systems: In fitro Permeability and In Vivo Oral Absorption of Salmon Calcitonin (sCT). Pharmaceutical Research, (1999), 16(4):527-533.
Song et al, Enhanced intestinal absorption of salmon calcitonin (sCT) from proliposomes containing bile salts. Journal of Controlled Release, (2005), 106: 298-308.
De La Fuente et al., Nanoparticles as protein and gene carriers to mucosal surfaces. Nanomedicine, (2008), 3(6): 845-857.
Caliceti et al, Development and in vivo evaluation of an oral insulin-PEG delivery system. European Journal of Pharmaceutical Sciences, (2004), 22:315-323.
Bernkop-Schnurch et al., The use of thiolated polymers as carrier matrix in oral peptide delivery—Proof of concept. Journal of Controlled Release, (2005), 106:26-33.
Shen et al., Intestinal Patches for Oral Drug Delivery. Pharmaceutical Research, (2002),19(4): 391-395.
Kusakabe et al., Amylin improves the effect of leptin on insulin sensitivity in leptin-resistant diet-induced obese miceAm J Physiol Endocrinol Metab, (2012), 302: E924-E931.
Nishizawa et al., Calcium/Calmodulin-mediated Action of Calcitonin on Lipid Metabolism in Rats. J Clin Invest., (1988), 82:1165-1172.

\* cited by examiner

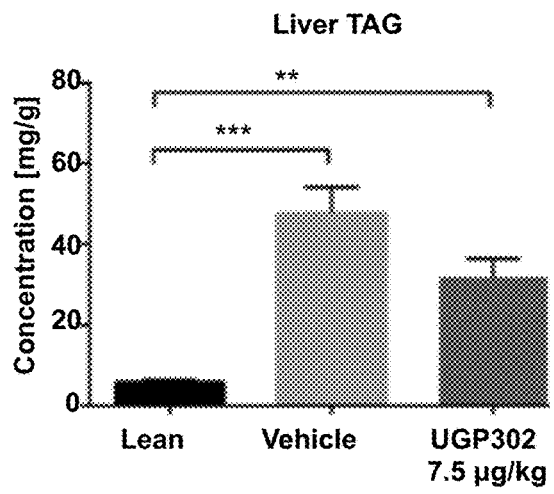
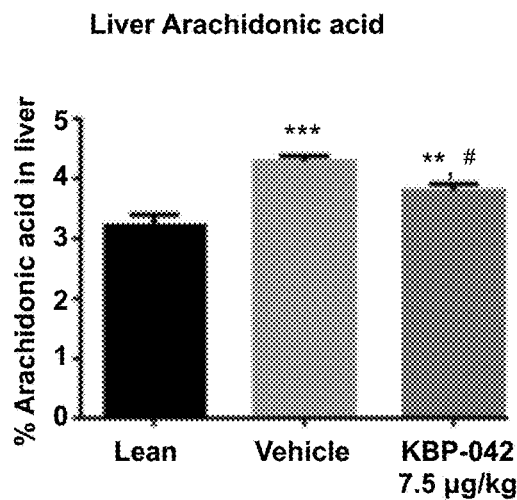
FIGURE 2A
FIGURE 2B
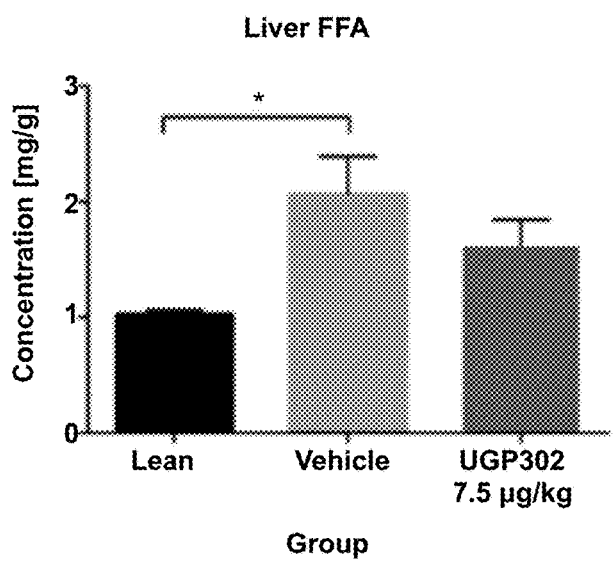
FIGURE 3

FIGURE 8A
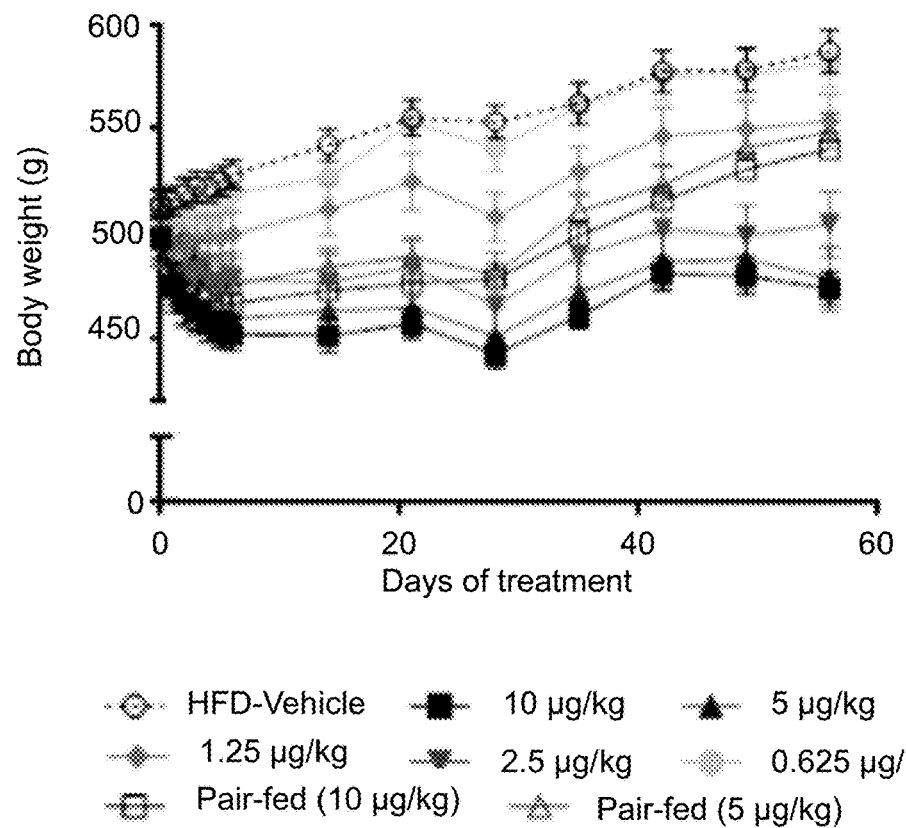
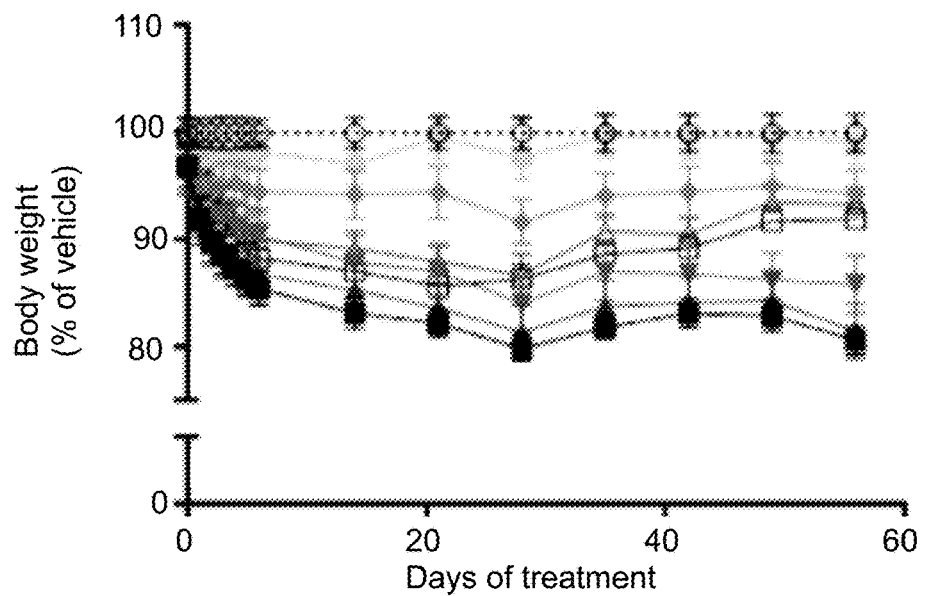
FIGURE 8B

| | ND-Control | STDEV | Vehicle | STDEV | 0.625 μg/kg | STDEV | 1.25 μg/kg | STDEV | 2.5 μg/kg | STDEV | 5 μg/kg | STDEV | 10 μg/kg | STDEV | Pair-fed 5 μg/kg | STDEV | Pair-fed 10 μg/kg | STDEV |
|---|---|---|---|---|---|---|---|---|---|---|---|---|---|---|---|---|---|---|
| C14:0 | 0.121 | 0.144 | 0.172 | 0.094 | 0.186 | 0.056 | 0.147 | 0.076 | 0.139 | 0.093 | 0.135 | 0.057 | 0.105 | 0.068 | 0.211 | 0.172 | 0.161 | 0.055 |
| C15:0 | 0.089 | 0.050 | 0.095 | 0.028 | 0.132 | 0.040 | 0.101 | 0.034 | 0.092 | 0.028 | 0.087 | 0.038 | 0.085 | 0.042 | 0.115 | 0.024 | 0.117 | 0.066 |
| C16:0 | 3.756 | 3.848 | 7.287 | 4.190 | 7.434 | 2.281 | 5.255 | 2.930 | 4.927 | 2.784 | 5.142 | 2.175 | 4.106 | 2.987 | 7.255 | 3.731 | 6.340 | 1.918 |
| C18:0 | 0.764 | 1.185 | 1.082 | 0.469 | 1.149 | 0.441 | 0.847 | 0.338 | 0.967 | 0.808 | 0.916 | 0.461 | 0.720 | 0.413 | 1.642 | 1.518 | 1.358 | 0.862 |
| C18:1n9 | 4.327 | 6.305 | 9.204 | 5.221 | 8.908 | 3.179 | 6.134 | 3.512 | 6.652 | 4.290 | 6.966 | 2.720 | 5.016 | 3.661 | 10.051 | 7.602 | 7.898 | 2.683 |
| C18:1 n7 | 0.381 | 0.356 | 0.538 | 0.293 | 0.610 | 0.204 | 0.447 | 0.204 | 0.481 | 0.290 | 0.462 | 0.172 | 0.357 | 0.220 | 0.559 | 0.263 | 0.486 | 0.146 |
| C18:3 n6 | 0.003 | 0.007 | 0.023 | 0.032 | 0.028 | 0.048 | 0.006 | 0.008 | 0.008 | 0.007 | 0.006 | 0.006 | 0.068 | 0.112 | 0.014 | 0.029 | 0.009 | 0.007 |
| C18:3 n3 | 0.191 | 0.156 | 0.299 | 0.176 | 0.284 | 0.099 | 0.197 | 0.133 | 0.169 | 0.116 | 0.189 | 0.095 | 0.168 | 0.131 | 0.309 | 0.166 | 0.273 | 0.091 |
| C20:4 n6 | 0.063 | 0.074 | 0.154 | 0.103 | 0.155 | 0.040 | 0.114 | 0.073 | 0.116 | 0.057 | 0.123 | 0.052 | 0.102 | 0.085 | 0.115 | 0.031 | 0.127 | 0.032 |
| C20:5 n3 | 0.582 | 0.579 | 1.231 | 0.723 | 1.393 | 0.391 | 0.851 | 0.468 | 0.855 | 0.383 | 0.875 | 0.335 | 0.761 | 0.571 | 1.099 | 0.373 | 1.309 | 0.795 |
| C22:4 n6 | 0.055 | 0.027 | 0.065 | 0.045 | 0.067 | 0.030 | 0.046 | 0.027 | 0.038 | 0.023 | 0.053 | 0.032 | 0.051 | 0.041 | 0.048 | 0.021 | 0.058 | 0.019 |
| C22:5 n6 | 0.160 | 0.197 | 0.409 | 0.290 | 0.391 | 0.137 | 0.248 | 0.193 | 0.230 | 0.135 | 0.244 | 0.095 | 0.231 | 0.188 | 0.332 | 0.140 | 0.337 | 0.084 |
| C22:5 n3 | 0.057 | 0.057 | 0.138 | 0.088 | 0.136 | 0.051 | 0.092 | 0.059 | 0.085 | 0.052 | 0.085 | 0.030 | 0.113 | 0.134 | 0.124 | 0.076 | 0.128 | 0.047 |
| C22:6 n3 | 0.124 | 0.115 | 0.221 | 0.147 | 0.230 | 0.068 | 0.149 | 0.108 | 0.135 | 0.074 | 0.158 | 0.080 | 0.152 | 0.127 | 0.207 | 0.054 | 0.225 | 0.062 |
| C22:6 n-3 | 0.148 | 0.120 | 0.296 | 0.187 | 0.299 | 0.082 | 0.198 | 0.135 | 0.176 | 0.111 | 0.159 | 0.070 | 0.170 | 0.146 | 0.252 | 0.104 | 0.308 | 0.235 |

FIGURE 9

CALCITONIN ANALOGUES FOR TREATING DISEASES AND DISORDERS

The present invention relates to analogues or mimetics of calcitonin, and their use in reducing accumulation of fats in the liver of subjects.

Calcitonins of natural occurrence from various species and analogues of the natural calcitonins have been proposed as medicaments in the treatment of various diseases and disorders, including, but not limited to diabetes (Type I and Type II), excess bodyweight, excessive food consumption and metabolic syndrome, the regulation of blood glucose levels, the regulation of response to glucose tolerance tests, the regulation of food intake, the treatment of osteoporosis and the treatment of osteoarthritis.

We have now found that certain analogues of natural calcitonins have an unexpected effect in reducing accumulation of triglycerides (fats) in the liver.

WO2013/067357 discloses synthetic variants of natural calcitonins having modified amino acid sequences which are intended to provide improved properties.

GB1320112.4 discloses further advantageous analogues of calcitonin.

Kusakabe et al (2011) examined the effect on tissue triglyceride content of a combination of amylin and leptin (L/A). L/A coadministration was found to decrease tissue triglyceride content significantly. The amylin dosage was 100 μg kg$^{-1}$. However, when administered alone, neither L nor A decreased tissue triglyceride contents compared with saline.

Nishizawa et al 1988 disclosed that synthetic salmon calcitonin injected subcutaneously into rats as a single dose of 1000 mU/rat (1 IU=25 μg) or over 12 weeks dose dependently (0.5-50 mU/rat) reduced triglyceride levels, lipoprotein levels and cholesterol levels in serum.

They also showed that the calcitonin reduced incorporation of acetate into cholesterol and triglycerides in cultured rat hepatocytes.

There is an ongoing need to develop more effective treatments to reduce tissue triglycerides, especially liver triglycerides.

The present invention now provides a calcitonin analogue as a medicament for producing a decrease in liver triglycerides or for reducing fat accumulation in the liver of a subject, wherein the calcitonin analogue is in SEQ ID NO:1 is C $X^1$ S L S T C $X^2$ L G $X^3$ L $X^4$ Q $X^5$ L H $X^6$ L Q $X^7$ $X^8$ P $X^9$ T D V G $X^{10}$ N A $X^{11}$ accordance with SEQ ID NO:1 or SEQ ID NO:2, where:
wherein, independently, $X^1$ is A or S; $X^2$ is V or M; $X^3$ is K or R; $X^4$ is either S or T, $X^5$ is either D or E; $X^6$ is K or R; $X^7$ is T or S; $X^8$ is F or Y; $X^9$ is K or R; $X^{10}$ is A or S; and $X^{11}$ is P or Y, P being preferred and SEQ ID NO:2 is C S N L S T C $X^2$ L G $X^3$ L S Q $X^5$ L H $X^6$ L Q $X^7$ $X^8$ P $X^9$ T D V G $X^{10}$ N $X^{12}$ $X^{11}$ wherein, independently, $X^2$ is V or M; $X^3$ is K or R; $X^5$ is D or E; $X^6$ is K or R; $X^7$ is T or S; $X^8$ is F or Y; $X^9$ is K or R; $X^{10}$ is A or S; $X^{12}$ is T or A, and $X^{11}$ is P or Y, P being preferred and wherein each said peptide sequence may be carboxylated at its N-terminal or otherwise modified to reduce the positive charge of the first amino acid and independently of that may be amidated at its C-terminal, and in each of which the 1 and 7 position cysteine residues may together be replaced by α-aminosuberic acid (Asu).

Preferred peptide sequences for use in the invention include:

SEQ ID NO:3 C A S L S T C $X^2$ L G $X^3$ L $X^4$ Q $X^5$ L H $X^6$ L Q $X^7$ $X^8$ P $X^9$ T D V G $X^{18}$ N A $X^{11}$ wherein, independently, $X^2$ is V or M; $X^3$ is K or R; $X^4$ is either S or T, $X^5$ is either D or E; $X^6$ is K or R; $X^7$ is T or S; $X^8$ is F or Y; $X^9$ is K or R; $X^{10}$ is A or S; and $X^{11}$ is P or Y, P being preferred, SEQ ID NO:4 C A S L S T C M L G R L S Q $X^5$ L H R L Q $X^7$ $X^8$ P K T D V G A N A $X^{11}$ wherein, independently, $X^5$ is either D or E; $X^7$ is T or S; $X^8$ is F or Y; and $X^{11}$ is P or Y, P being preferred, SEQ ID NO:5 C S N L S T C V L G $X^3$ L S Q E L H $X^6$ L Q T $X^8$ P R T D V G A N $X^{12}$ $X^{11}$ wherein, independently, $X^3$ is K or R; $X^6$ is K or R; $X^8$ is F or Y; $X^{12}$ is T or A, and $X^{11}$ is P or Y, P being preferred; all of which may be modified as described above.

Other preferred peptides for use in the invention include:

```
                                         SEQ ID NO: 6
CASLSTCVLGRLSQXcLHRLQIXePRTDVGANAP

SEQ ID NO: 7
CASLSTCMLGKLIQXcLHKLQIXePRTDVGANAP

SEQ ID NO: 8
(KBP-056/057)CASLSTCVLGKLSQXcLHKLQIXePKTDVGANAP

SEQ ID NO: 9
(KBP-088/089)CSNLSTCMLGRLSQXcLHRLQIXePKTDVGANAP

SEQ ID NO: 10
CASLSTCMLGRLSQXcLHRLQIXePKTDVGANAP

SEQ ID NO: 11
CASLSTCMLGKLIQXcLHKLQIXePKTDVGANAP

SEQ ID NO: 12
CASLSTCVLGKLSQXcLHKLQIXePRTDVGANAP

SEQ ID NO: 13
CSNLSTCVLGRLSQXcLHRLQIXePKTDVGANAP

SEQ ID NO: 14
(KBP-017)CASLSTCVLGKLSQXcLHKLQSXePKTDVGANAP

SEQ ID NO: 15
(KBP-018)CASLSTCVLGKLSQXcLHKLQIXePKTDVGANAP
``` wherein $X^c$ is either D or E and $X^e$ is independently either F or Y and each of which sequences may be carboxylated at its N-terminal or otherwise modified to reduce the positive charge of the first amino acid and independently of that may be amidated at its C-terminal, and in each of which the 1 and 7 position cysteine residues may together be replaced by α-aminosuberic acid (Asu).

Other preferred peptides for use in the invention include:

```
                                         SEQ ID NO: 16
(KBP-011)CASLSTCVLGRLSQELHRLQTFPRTDVGANAP

SEQ ID NO: 17
CASLSTCMLGKLTQELHKLQTFPRTDVGANAP

SEQ ID NO: 18
(KBP-018)CASLSTCVLGKLSQELHKLQTFPKTDVGANAP

SEQ ID NO: 19
(KBP-088)CSNLSTCMLGRLSQELHRLQTFPKTDVGANAP

SEQ ID NO: 20
CASLSTCVLGRLSQELHRLQTYPRTDVGANAP

SEQ ID NO: 21
CASLSTCMLGKLTQELHKLQTYPRTDVGANAP

SEQ ID NO: 22
CASLSTCVLGKLSQELHKLQTYPKTDVGANAP

SEQ ID NO: 23
(KBP-021)CSNLSTCMLGRLSQELHRLQTYPKTDVGANAP

SEQ ID NO: 24
CASLSTCVLGRLSQDLHRLQTFPRTDVGANAP
```

```
                                                SEQ ID NO: 25
CASLSTCMLGKLTQDLHKLQTFPRTDVGANAP

SEQ ID NO: 26
(KBP-056) CASLSTCVLGKLSQDLHKLQTFPKTDVGANAP

SEQ ID NO: 27
CSNLSTCMLGRLSQDLHRLQTFPKTDVGANAP

SEQ ID NO: 28
CASLSTCVLGRLSQDLHRLQTYPRTDVGANAP

SEQ ID NO: 29
CASLSTCMLGKLTQDLHKLQTYPRTDVGANAP

SEQ ID NO: 30
(KBP-057) CASLSTCVLGKLSQDLHKLQTYPKTDVGANAP

SEQ ID NO: 31
(KBP-089) CSNLSTCMLGRLSQDLHRLQTYPKTDVGANAP

SEQ ID NO: 32
CASLSTCVLGRLSQELHRLQSFPRTDVGANAP

SEQ ID NO: 33
CASLSTCMLGKLTQELHKLQSFPRTDVGANAP

SEQ ID NO: 34
CASLSTCVLGKLSQELHKLQSFPKTDVGANAP

SEQ ID NO: 35
CSNLSTCMLGRLSQELHRLQSFPKTDVGANAP

SEQ ID NO: 36
CASLSTCVLGRLSQELHRLQSYPRTDVGANAP

SEQ ID NO: 37
CASLSTCMLGKLTQELHKLQSYPRTDVGANAP

SEQ ID NO: 38
CASLSTCVLGKLSQELHKLQSYPKTDVGANAP

SEQ ID NO: 39
CSNLSTCMLGRLSQELHRLQSYPKTDVGANAP

SEQ ID NO: 40
CASLSTCVLGRLSQDLHRLQSFPRTDVGANAP

SEQ ID NO: 41
CASLSTCMLGKLTQDLHKLQSFPRTDVGANAP

SEQ ID NO: 42
CASLSTCVLGKLSQDLHKLQSFPKTDVGANAP

SEQ ID NO: 43
CSNLSTCMLGRLSQDLHRLQSFPKTDVGANAP

SEQ ID NO: 44
CASLSTCVLGRLSQDLHRLQSYPRTDVGANAP

SEQ ID NO: 45
CASLSTCMLGKLTQDLHKLQSYPRTDVGANAP

SEQ ID NO: 46
(KBP-017) CASLSTCVLGKLSQDLHKLQSYPKTDVGANAP

SEQ ID NO: 47
CSNLSTCMLGRLSQDLHRLQSYPKTDVGANAP

SEQ ID NO: 48
CSNLSTCVLGKLSQELHKLQTYPKTDVGANAP

SEQ ID NO: 49
(KBP-019) CASLSTCMLGRLSQDLHRLQTYPKTDVGANAP
``` which may be modified as described above.

```
                                                SEQ ID NO: 50
(KBP-011) AcCASLSTCVLGRLSQELHRLQTFPRTDVGANAP-NH2

SEQ ID NO: 51
(KBP-017) AcCASLSTCVLGKLSQDLHKLQSYPKTDVGANAP-NH2

SEQ ID NO: 52
(KBP-018) AcCASLSTCVLGKLSQELHKLQTFPKTDVGANAP-NH2

SEQ ID NO: 53
(KBP-023) AcCASLSTCMLGKLTQELHKLQTFPRTDVGANAP-NH2

SEQ ID NO: 54
(KBP-042) AcCSNLSTCVLGKLSQELHKLQTYPRTDVGANAP-NH2

SEQ ID NO: 55
(KBP-056) AcCASLSTCVLGKLSQDLHKLQTFPKTDVGANAP-NH2

SEQ ID NO: 56
(KBP-057) AcCASLSTCVLGKLSQDLHKLQTYPKTDVGANAP-NH2

SEQ ID NO: 57
(KBP-088) AcCSNLSTCMLGRLSQELHRLQTFPKTDVGANAP-NH2

SEQ ID NO: 58
(KBP-089) AcCSNLSTCMLGRLSQDLHRLQTYPKTDVGANAP-NH2
```

Other preferred peptides for use in the invention include:

```
                                                SEQ ID NO: 59
CASLSTCVLGRLSQX^c LHRLQTX^e PKTDVGANAY

SEQ ID NO: 60
CASLSTCMLGKLIQX^c LHKLQIX^e PKTDVGANAY

SEQ ID NO: 61
CASLSTCVLGKLSQX^c LHKLQTX^e PKTDVGANAY

SEQ ID NO: 62
CSNLSTCMLGRLSQX^c LHRLQTX^e PKTDVGANAY

SEQ ID NO: 63
CASLSTCVLGRLSQX^c LHRLQTX^e PRTDVGANAY

SEQ ID NO: 64
CASLSTCMLGKLIQX^c LHKLQIX^e PRTDVGANAY

SEQ ID NO: 65
CASLSTCVLGRLSQX^c LHRLQTX^e PKTDVGANAP

SEQ ID NO: 66
CASLSTCMLGKLIQX^c LHKLQIX^e PKTDVGANAP
``` wherein $X^c$ is either D or E and $X^e$ is independently either F or Y, any of which may be modified as described above.

Other preferred peptides for use in the invention include:

```
                                                SEQ ID NO: 67
CASLSTCVLGRLSQELHRLQTFPKTDVGANAY

SEQ ID NO: 68
CASLSTCMLGKLTQELHKLQTFPKTDVGANAY

SEQ ID NO: 69
CASLSTCVLGKLSQDLHKLQTFPKTDVGANAY

SEQ ID NO: 70
CSNLSTCMLGRLSQELHRLQTFPKTDVGANAY

SEQ ID NO: 71
CASLSTCVLGRLSQELHRLQTFPRTDVGANAY

SEQ ID NO: 72
CASLSTCMLGKLTQELHKLQTFPRTDVGANAY

SEQ ID NO: 73
CASLSTCVLGRLSQELHRLQTFPKTDVGANAP

SEQ ID NO: 74
CASLSTCMLGKLTQELHKLQTFPKTDVGANAP
``` any of which may be modified as described above.

The peptide may be formulated for administration as a pharmaceutical and may be formulated for enteral or parenteral administration. Preferred formulations are injectable, preferably for subcutaneous injection, however the peptide may be formulated with a carrier for oral administration, and optionally wherein the carrier increases the oral bioavailability of the peptide. Suitable carriers include ones that comprise 5-CNAC, SNAD, or SNAC.

Optionally, the peptide is formulated in a pharmaceutical composition for oral administration comprising coated citric acid particles, and wherein the coated citric acid particles increases the oral bioavailability of the peptide.

The invention includes a peptide of the invention for use as a medicament. The peptide may be for use in treating diabetes (Type I and/or Type II), excess bodyweight, excessive food consumption, metabolic syndrome, rheumatoid arthritis, non-alcoholic fatty liver disease, osteoporosis, or osteoarthritis, poorly regulated blood glucose levels, poorly regulated response to glucose tolerance tests, or poorly regulated of food intake. In particular, the peptides may be used to lower an undesirably high fasting blood glucose level or to lower an undesirably high HbA1c or to reduce an undesirably high response to a glucose tolerance test. Preferably, peptides of the invention may be used for producing a decrease in liver triglycerides and/or for reducing fat accumulation in the liver of a subject whilst simultaneously reducing the food intake and/or body weight of the subject.

In some embodiments, the N-terminal side of the calcitonin mimetics discussed supra is modified to reduce the positive charge of the first amino acid. For example, an acetyl, propionyl, or succinyl group may be substituted on cysteine-1. Herein, "Ac" refers to an acetyl group modification. Each 'Ac' may be replaced by "Pr" referring to a propionyl group modification, or by "Succ" referring to a succinyl group modification. "$NH_2$" refers to an amidated C-terminal carboxylic acid group. Alternative ways of reducing positive charge include, but are not limited to, polyethylene glycol-based PEGylation, or the addition of another amino acid such as glutamic acid or aspartic acid at the N-terminus. Alternatively, other amino acids may be added to the N-terminus of peptides discussed supra including, but not limited to, lysine, glycine, formylglycine, leucine, alanine, acetyl alanine, and dialanyl. As those of skill in the art will appreciate, peptides having a plurality of cysteine residues frequently form a disulfide bridge between two such cysteine residues. All such peptides set forth herein are defined as optionally including one or more such disulphide bridges, particularly at the Cys1-Cys7 locations. Mimicking this, the cysteines at positions 1 and 7 may jointly be replaced by an α-aminosuberic acid linkage. All peptides disclosed herein that have KBP-0## numbers have such a disulphide bridge.

While calcitonin mimetics of the present disclosure may exist in free acid form, it is preferred that the C-terminal amino acid be amidated. Applicants expect that such amidation may contribute to the effectiveness and/or bioavailability of the peptide. A preferred technique for manufacturing amidated versions of the calcitonin mimetics of the present disclosure is to react precursors (having glycine in place of the C-terminal amino group of the desired amidated product) in the presence of peptidylglycine alpha-amidating monooxygenase in accordance with known techniques wherein the precursors are converted to amidated products in reactions described, for example, in U.S. Pat. No. 4,708,934 and EP0308067 and EP0382403.

Recombinant production is preferred for both the precursor and the enzyme that catalyzes the conversion of the precursor to salmon calcitonin. Such recombinant production is discussed in Biotechnology, Vol. 11 (1993) pp. 64-70, by Ray M V, Van Duyne P, Bertelsen A H, Jackson-Matthews D E, Sturmer A M, Merkler D J, Consalvo A P, Young S D, Gilligan J P, Shields P P. which further describes a conversion of a precursor to an amidated product. The recombinant product reported there is identical to natural salmon calcitonin, and to salmon calcitonin produced using solution and solid phase chemical peptide synthesis.

Production of amidated products may also be accomplished using the process and amidating enzyme set forth by Consalvo, et al in U.S. Pat. No. 7,445,911; Miller et al, US2006/0292672; Ray et al, 2002, Protein Expression and Purification, 26:249-259; and Mehta, 2004, Biopharm. International, July, pp. 44-46.

The production of the preferred amidated peptides may proceed, for example, by producing glycine-extended precursor in E. coli as a soluble fusion protein with glutathione-S-transferase, or by direct expression of the precursor in accordance with the technique described in U.S. Pat. No. 6,103,495. Such a glycine extended precursor has a molecular structure that is identical to the desired amidated product except at the C-terminus (where the product terminates —X—$NH_2$, while the precursor terminates —X-gly, X being the C-terminal amino acid residue of the product). An alpha-amidating enzyme described in the publications above catalyzes conversion of precursors to product. That enzyme is preferably recombinantly produced, for example, in Chinese Hamster Ovary (CHO) cells), as described in the Biotechnology and Biopharm. articles cited above.

Free acid forms of peptide active agents of the present disclosure may be produced in like manner, except without including a C-terminal glycine on the "precursor", which precursor is instead the final peptide product and does not require the amidation step.

Except where otherwise stated, the preferred dosage of the calcitonin mimetics of the present disclosure is identical for both therapeutic and prophylactic purposes. Desired dosages are discussed in more detail, infra, and differ depending on mode of administration.

Except where otherwise noted or where apparent from context, dosages herein refer to weight of active compounds unaffected by or discounting pharmaceutical excipients, diluents, carriers or other ingredients, although such additional ingredients are desirably included. Any dosage form (capsule, tablet, injection or the like) commonly used in the pharmaceutical industry for delivery of peptide active agents is appropriate for use herein, and the terms "excipient", "diluent", or "carrier" includes such non-active ingredients as are typically included, together with active ingredients in such dosage form in the industry. A preferred oral dosage form is discussed in more detail, infra, but is not to be considered the exclusive mode of administering the active agents of the present disclosure.

The calcitonin mimetics of the present disclosure can be administered to a patient to treat a number of diseases or disorders. As used herein, the term "patient" means any organism belonging to the kingdom Animalia. In an embodiment, the term "patient" refers to vertebrates, more preferably, mammals including humans.

There are a number of art-recognized measures of normal range for body weight in view of a number of factors such as gender, age and height. A patient in need of treatment or prevention regimens set forth herein include patients whose body weight exceeds recognized norms or who, due to heredity, environmental factors or other recognized risk factor, are at higher risk than the general population of becoming overweight or obese. In accordance with the present disclosure, it is contemplated that the calcitonin mimetics may be used to treat diabetes where weight control is an aspect of the treatment.

In an embodiment, the method includes enteral administration to a patient in need thereof for treatment of a said condition of a pharmaceutically effective amount of any one of the peptides described herein.

In an embodiment, the method includes parenteral administration to a patient in need thereof for treatment of a said condition of a pharmaceutically effective amount of any one of the peptides described herein. For parenteral administration (including intraperitoneal, subcutaneous, intravenous, intradermal or intramuscular injection), solutions of a peptide of the present disclosure in either sesame or peanut oil or in aqueous propylene glycol may be employed, for example. The aqueous solutions should be suitably buffered (preferably pH greater than 8) if necessary and the liquid diluent first rendered isotonic. These aqueous solutions are suitable for intravenous injection purposes. The oily solutions are suitable for intraarticular, intramuscular and subcutaneous injection purposes. The preparation of all these solutions under sterile conditions is readily accomplished by standard pharmaceutical techniques well known to those skilled in the art. For parenteral application, examples of suitable preparations include solutions, preferably oily or aqueous solutions as well as suspensions, emulsions, or implants, including suppositories. Peptides may be formulated in sterile form in multiple or single dose formats such as being dispersed in a fluid carrier such as sterile physiological saline or 5% saline dextrose solutions commonly used with injectables.

Said method may include a preliminary step of determining whether the patient suffers from a said condition, and/or a subsequent step of determining to what extent said treatment is effective in mitigating the condition in said patient, e.g. in each case, carrying out an oral glucose tolerance test or a resting blood sugar level.

For improved control over the weight of the patient, to produce a loss of weight or an avoidance of weight gain, the active compound is preferably administered once daily or more such as at least twice per day, e.g. from 2-4 times per day. Formulations of the active compound may contain a unit dosage appropriate for such an administration schedule. The active compounds may be administered with a view to controlling the weight of a patient undergoing treatment for diabetes or metabolic syndrome.

Oral enteral formulations are for ingestion by swallowing for subsequent release in the intestine below the stomach, and hence delivery via the portal vein to the liver, as opposed to formulations to be held in the mouth to allow transfer to the bloodstream via the sublingual or buccal routes.

Suitable dosage forms for use in the present disclosure include tablets, mini-tablets, capsules, granules, pellets, powders, effervescent solids and chewable solid formulations. Such formulations may include gelatin which is preferably hydrolysed gelatin or low molecular weight gelatin. Such formulations may be obtainable by freeze drying a homogeneous aqueous solution comprising calcitonin or a fragment or conjugate thereof and hydrolysed gelatin or low molecular weight gelatin and further processing the resulting solid material into said oral pharmaceutical formulation, and wherein the gelatin may have a mean molecular weight from 1000 to 15000 Daltons. Such formulations may include a protective carrier compound such as 5-CNAC or others as disclosed herein.

Whilst oral formulations such as tablets and capsules are preferred, compositions for use in the present disclosure may take the form of syrups, elixirs or the like and suppositories or the like. Oral delivery is generally the delivery route of choice since it is convenient, relatively easy and generally painless, resulting in greater patient compliance relative to other modes of delivery. However, biological, chemical and physical barriers such as varying pH in the gastrointestinal tract, powerful digestive enzymes, and active agent impermeable gastrointestinal membranes, makes oral delivery of calcitonin like peptides to mammals problematic, e.g. the oral delivery of calcitonins, which are long-chain polypeptide hormones secreted by the parafollicular cells of the thyroid gland in mammals and by the ultimobranchial gland of birds and fish, originally proved difficult due, at least in part, to the insufficient stability of calcitonin in the gastrointestinal tract as well as the inability of calcitonin to be readily transported through the intestinal walls into the blood stream.

Suitable oral formulations are however described below.

Treatment of Patients

In an embodiment, a calcitonin mimetic of the present disclosure is administered at adequate dosage to maintain serum levels of the mimetic in patients between 5 picograms and 500 nanograms per milliliter, preferably between 50 picograms and 250 nanograms, e.g. between 1 and 100 nanograms per milliliter. The serum levels may be measured by radioimmunoassay techniques known in the art. The attending physician may monitor patient response, and may then alter the dosage somewhat to account for individual patient metabolism and response. Near simultaneous release is best achieved by administering all components of the present disclosure as a single pill or capsule. However, the disclosure also includes, for example, dividing the required amount of the calcitonin mimetic among two or more tablets or capsules which may be administered together such that they together provide the necessary amount of all ingredients. "Pharmaceutical composition," as used herein includes but is not limited to a complete dosage appropriate to a particular administration to a patient regardless of whether one or more tablets or capsules (or other dosage forms) are recommended at a given administration.

A calcitonin mimetic of the present disclosure may be formulated for oral administration using the methods employed in the Unigene Enteripep® products. These may include the methods as described in U.S. Pat. Nos. 5,912,014, 6,086,918, 6,673,574, 7,316,819, 8,093,207, and US Publication No. 2009/0317462. In particular, it may include the use of conjugation of the compound to a membrane translocator such as the protein transduction domain of the HIV TAT protein, co-formulation with one or more protease inhibitors, and/or a pH lowering agent which may be coated and/or an acid resistant protective vehicle and/or an absorption enhancer which may be a surfactant.

In an embodiment, a calcitonin mimetic of the present disclosure is preferably formulated for oral delivery in a manner known in U.S. Patent Publication No. 2009/0317462. One preferred oral dosage form in accordance with the present disclosure is set forth in the Table below:

| COMPONENTS OF A SOLID DOSAGE FORMULATION | |
|---|---|
| ACTIVE AGENT OR EXCIPIENT | FUNCTION |
| A Calcitonin Mimetic selected from one of SEQ ID NO: 1-8 | Active agent |
| Coated Citric Acid Particles | Protease Inhibitor |
| Lauroylcarnitine | Absorption Enhancer |
| Nonionic Polymer | Subcoat |
| Eudragit L30D-55 | Enteric Coat |

In an embodiment, a calcitonin mimetic of the present disclosure may be formulated for enteral, especially oral, administration by admixture with a suitable carrier compound. Suitable carrier compounds include those described in U.S. Pat. Nos. 5,773,647 and 5,866,536 and amongst these, 5-CNAC (N-(5-chlorosalicyloyl)-8-aminocaprylic acid, commonly as its disodium salt) is particularly effective. Other preferred carriers or delivery agents are SNAD (sodium salt of 10-(2-Hydroxybenzamido)decanoic acid) and SNAC (sodium salt of N-(8-[2-hydroxybenzoyl]amino) caprylic acid). In an embodiment, a pharmaceutical composition of the present disclosure comprises a delivery effective amount of carrier such as 5-CNAC, i.e. an amount sufficient to deliver the compound for the desired effect. Generally, the carrier such as 5-CNAC is present in an amount of 2.5% to 99.4% by weight, more preferably 25% to 50% by weight of the total composition.

In addition, WO 00/059863 discloses the disodium salts of formula I

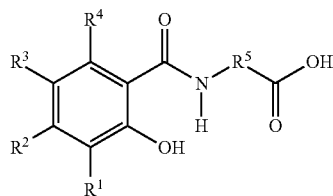

wherein

R$^1$, R$^2$, R$^3$, and R$^4$ are independently hydrogen, —OH, —NR$^6$R$^7$, halogen, C$_1$-C$_4$ alkyl, or C$_1$-C$_4$ alkoxy;

R$^5$ is a substituted or unsubstituted C$_2$-C$_{16}$ alkylene, substituted or unsubstituted C$_2$-C$_{16}$ alkenylene, substituted or unsubstituted C$_1$-C$_{12}$ alkyl(arylene), or substituted or unsubstituted aryl (C$_1$-C$_{12}$ alkylene); and R$^6$ and R$^7$ are independently hydrogen, oxygen, or C$_1$-C$_4$ alkyl; and hydrates and solvates thereof as particularly efficacious for the oral delivery of active agents, such as calcitonins, e.g. salmon calcitonin, and these may be used in the present disclosure.

Preferred enteric formulations using optionally micronised 5-CNAC may be generally as described in WO2005/014031.

The compound may be formulated for oral administration using the methods employed in the Capsitonin product of Bone Medical Limited. These may include the methods incorporated in Axcess formulations. More particularly, the active ingredient may be encapsulated in an enteric capsule capable of withstanding transit through the stomach. This may contain the active compound together with a hydrophilic aromatic alcohol absorption enhancer, for instance as described in WO02/028436. In a known manner the enteric coating may become permeable in a pH sensitive manner, e.g. at a pH of from 3 to 7. WO2004/091584 also describes suitable formulation methods using aromatic alcohol absorption enhancers.

The compound may be formulated using the methods seen in the Oramed products, which may include formulation with omega-3 fatty acid as seen in WO2007/029238 or as described in U.S. Pat. No. 5,102,666.

Generally, the pharmaceutically acceptable salts (especially mono or di sodium salts), solvates (e.g. alcohol solvates) and hydrates of these carriers or delivery agents may be used.

Oral administration of the pharmaceutical compositions according to the disclosure can be accomplished regularly, e.g. once or more on a daily or weekly basis; intermittently, e.g. irregularly during a day or week; or cyclically, e.g. regularly for a period of days or weeks followed by a period without administration. The dosage form of the pharmaceutical compositions of the presently disclosed embodiments can be any known form, e.g. liquid or solid dosage forms. The liquid dosage forms include solution emulsions, suspensions, syrups and elixirs. In addition to the active compound and carrier such as 5-CNAC, the liquid formulations may also include inert excipients commonly used in the art such as, solubilizing agents e.g. ethanol; oils such as cottonseed, castor and sesame oils; wetting agents; emulsifying agents; suspending agents; sweeteners; flavourings; and solvents such as water. The solid dosage forms include capsules, soft-gel capsules, tablets, caplets, powders, granules or other solid oral dosage forms, all of which can be prepared by methods well known in the art. The pharmaceutical compositions may additionally comprise additives in amounts customarily employed including, but not limited to, a pH adjuster, a preservative, a flavorant, a taste-masking agent, a fragrance, a humectant, a tonicifier, a colorant, a surfactant, a plasticizer, a lubricant such as magnesium stearate, a flow aid, a compression aid, a solubilizer, an excipient, a diluent such as microcrystalline cellulose, e.g. Avicel PH 102 supplied by FMC corporation, or any combination thereof. Other additives may include phosphate buffer salts, citric acid, glycols, and other dispersing agents. The composition may also include one or more enzyme inhibitors, such as actinonin or epiactinonin and derivatives thereof; aprotinin, Trasylol and Bowman-Birk inhibitor. Further, a transport inhibitor, i.e. a [rho]-glycoprotein such as Ketoprofin, may be present in the compositions of the present disclosure. The solid pharmaceutical compositions of the instant disclosure can be prepared by conventional methods e.g. by blending a mixture of the active compound, the carrier such as 5-CNAC, and any other ingredients, kneading, and filling into capsules or, instead of filling into capsules, molding followed by further tableting or compression-molding to give tablets. In addition, a solid dispersion may be formed by known methods followed by further processing to form a tablet or capsule. Preferably, the ingredients in the pharmaceutical compositions of the instant disclosure are homogeneously or uniformly mixed throughout the solid dosage form.

Alternatively, the active compound may be formulated as a conjugate with said carrier, which may be an oligomer as described in US2003/0069170, e.g.

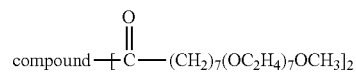

Such conjugates may be administered in combination with a fatty acid and a bile salt as described there.

Conujugates with polyethylene glycol (PEG) may be used, as described for instance in Mansoor et al.

Alternatively, active compounds may be admixed with nitroso-N-acetyl-D,L-penicillamine (SNAP) and Carbopol solution or with taurocholate and Carbapol solution to form a mucoadhesive emulsion.

The active compound may be formulated by loading into chitosan nanocapsules as disclosed in Prego et al (optionally PEG modified as in Prego Prego C, Torres D, Fernandez-Megia E, Novoa-Carballal R, Quiñoà E, Alonso M J.) or chitosan or PEG coated lipid nanoparticles as disclosed in Garcia-Fuentes et al. Chitosan nanoparticles for this purpose may be iminothiolane modified as described in Guggi et al. They may be formulated in water/oil/water emulsions as described in Dogru et al. The bioavailability of active compounds may be increased by the use of taurodeoxycholate or lauroyl carnitine as described in Sinko et al or in Song et al. Generally, suitable nanoparticles as carriers are discussed in de la Fuente et al and may be used in the present disclosure.

Other suitable strategies for oral formulation include the use of a transient permeability enhancer (TPE) system as described in WO2005/094785 of Chiasma Ltd. TPE makes use of an oily suspension of solid hydrophilic particles in a hydrophobic medium to protect the drug molecule from inactivation by the hostile gastrointestinal (GI) environment and at the same time acts on the GI wall to induce permeation of its cargo drug molecules.

Further included is the use of glutathione or compounds containing numerous thiol groups as described in US2008/0200563 to inhibit the action of efflux pumps on the mucous membrane. Practical examples of such techniques are described also in Caliceti, P. Salmaso, S., Walker, G. and Bernkop-Schnürch, A. (2004) 'Development and in vivo evaluation of an oral insulin-PEG delivery system.' Eur. J. Pharm. Sci., 22, 315-323, in Guggi, D., Krauland, A. H., and Bernkop-Schnürch, A. (2003) 'Systemic peptide delivery via the stomach: in vivo evaluation of an oral dosage form for salmon calcitonin'. J. Control. Rel. 92, 125-135, and in Bernkop-Schnürch, A., Pinter, Y., Guggi, D., Kahlbacher, H., Schöffmann, G., Schuh, M., Schmerold, I., Del Curto, M. D., D'Antonio, M., Esposito, P. and Huck, Ch. (2005) 'The use of thiolated polymers as carrier matrix in oral peptide delivery'—Proof of concept. J. Control. Release, 106, 26-33.

The active compound may be formulated in seamless micro-spheres as described in WO2004/084870 where the active pharmaceutical ingredient is solubilised as an emulsion, microemulsion or suspension formulated into minispheres; and variably coated either by conventional or novel coating technologies. The result is an encapsulated drug in "pre-solubilised" form which when administered orally provides for predetermined instant or sustained release of the active drug to specific locations and at specific rates along the gastrointestinal tract. In essence, pre-solubilization of the drug enhances the predictability of its kinetic profile while simultaneously enhancing permeability and drug stability.

One may employ chitosan coated nanocapsules as described in US2009/0074824. The active molecule administered with this technology is protected inside the nanocapsules since they are stable against the action of the gastric fluid. In addition, the mucoadhesive properties of the system enhances the time of adhesion to the intestine walls (it has been verified that there is a delay in the gastrointestinal transit of these systems) facilitating a more effective absorption of the active molecule.

Methods developed by TSR1 Inc. may be used. These include Hydrophilic Solubilization Technology (HST) in which gelatin, a naturally derived collagen extract carrying both positive and negative charges, coats the particles of the active ingredient contained in lecithin micelles and prevents their aggregation or clumping. This results in an improved wettability of hydrophobic drug particles through polar interactions. In addition, the amphiphilic lecithin reduces surface tension between the dissolution fluid and the particle surface.

The active ingredient may be formulated with cucurbiturils as excipients.

Alternatively, one may employ the GIPET technology of Merrion Pharmaceuticals to produce enteric coated tablets containing the active ingredient with an absorption enhancer which may be a medium chain fatty acid or a medium chain fatty acid derivative as described in US2007/0238707 or a membrane translocating peptide as described in U.S. Pat. No. 7,268,214.

One may employ GIRES™ technology which consists of a controlled-release dosage form inside an inflatable pouch, which is placed in a drug capsule for oral administration. Upon dissolution of the capsule, a gas-generating system inflates the pouch in the stomach. In clinical trials the pouch has been shown to be retained in the stomach for 16-24 hours.

Alternatively, the active may be conjugated to a protective modifier that allows it to withstand enzymatic degradation in the stomach and facilitate its absorption. The active may be conjugated covalently with a monodisperse, short-chain methoxy polyethylene glycol glycolipids derivative that is crystallized and lyophilized into the dry active pharmaceutical ingredient after purification. Such methods are described in U.S. Pat. No. 5,438,040 and at biocon.com.

One may also employ a hepatic-directed vesicle (HDV) for active delivery. An HDV may consist of liposomes (≤150 nm diameter) encapsulating the active, which also contain a hepatocyte-targeting molecule in their lipid bilayer. The targeting molecule directs the delivery of the encapsulated active to the liver cells and therefore relatively minute amounts of active are required for effect. Such technology is described in US2009/0087479 and further at diasome.com.

The active may be incorporated into a composition containing additionally a substantially non-aqueous hydrophilic medium comprising an alcohol and a cosolvent, in association with a medium chain partial glyceride, optionally in admixture with a long-chain PEG species as described in US2002/0115592 in relation to insulin.

Alternatively, use may be made of intestinal patches as described in Shen Z, Mitragotri S, Pharm Res. 2002 April; 19(4):391-5 'Intestinal patches for oral drug delivery'.

The active may be incorporated into an erodible matrix formed from a hydrogel blended with a hydrophobic polymer as described in U.S. Pat. No. 7,189,414.

Suitable dosage levels for adult humans to be treated may be in the range of from 0.001 µg/kg/day to 50 mg/kg/day. More preferably the dosage may be from 0.01 µg/kg/day to 5 mg/kg/day, more preferably from 0.1 µg/kg/day to 500 µg/kg/day. Such dosage ranges may be for the active component of an oral preparation or of a parenteral, e.g. injectable preparation. For oral or other enteral formulations, the dose may be 0.01 to 100 mg/kg/day, and for injectable or other parenteral formulations the dose may be from 0.01 to 1000 µg/kg/day.

The frequency of dosage treatment of patients may be from 1 to six times daily, for instance from two to four times daily. Treatment will desirably be maintained over a prolonged period of at least 6 weeks, preferably at least 6 months, preferably at least a year, and optionally for life.

Combination treatments for relevant conditions may be carried out using a composition according to the present disclosure and separate administration of one or more other therapeutics. Alternatively, the composition according to the present disclosure may incorporate one or more other therapeutics for combined administration.

Combination therapies according to the present disclosure include combinations of an active compound as described with insulin, GLP-2, GLP-1, GIP, or amylin, or generally with other anti-diabetics. Thus combination therapies including co-formulations may be made with insulin sensitizers including biguanides such as Metformin, Buformin and Phenformin, TZD's (PPAR) such as Balaglitazone, Pioglitazone, Rivoglitazone, Rosiglitazone and Troglitazone, dual PPAR agonists such as Aleglitazar, Muraglitazar and Tesaglitazar, or secretagogues including sulphonylureas such as Carbutamide, Chloropropamide, Gliclazide, Tolbutamide, Tolazamide, Glipizide, Glibenclamide, Glyburide, Gliquidone, Glyclopyramide and Glimepriride, Meglitinides/glinides (K+) such as Nateglinide, Repaglinide and Mitiglinide, GLP-1 analogs such as Exenatide, Liraglutide and Albiglutide, DPP-4 inhibitors such as Alogliptin, Linagliptin, Saxagliptin, Sitagliptin and Vildagliptin, insulin analogs or special formulations such as (fast acting) Insulin lispro, Insulin aspart, Insulin glulisine, (long acting) Insulin glargine, Insulin detemir), inhalable insulin—Exubra and NPH insulin, and others including alpha-glucosidase inhibitors such as Acarbose, Miglitol and Voglibose, amylin analogues such as Pramlintide, SGLT2 inhibitors such as Dapagliflozin, Remogliflozin and Sergliflozin as well as miscellaneous ones including Benfluorex and Tolrestat.

Further combinations include co-administration or co-formulation with leptins. Leptin resistance is a well-established component of type 2 diabetes; however, injections of leptin have so far failed to improve upon this condition. In contrast, there is evidence supporting that amylin, and thereby molecules with amylin-like abilities, as the salmon calcitonin mimetics, are able to improve leptin sensitivity. Amylin/leptin combination has shown a synergistic effect on body weight and food intake, and also insulin resistance [Kusakabe T et al].

The presently disclosed embodiments is described in the following Examples, which are set forth to aid in the understanding of the disclosure, and should not be construed to limit in any way the scope of the disclosure as defined in the claims which follow thereafter. The following examples are put forth so as to provide those of ordinary skill in the art with a complete disclosure and description of how to make and use the described embodiments, and are not intended to limit the scope of the present disclosure nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

The invention will be further illustrated and explained by the following non-limiting example which makes reference to the accompanying drawings in which:

FIGS. 2A-2B show liver triacylglycerols and arachidonic acid following 16-days of treatment in obese rats.

FIG. 3 shows liver free fatty acids following 16-days of treatment in obese rats.

Figure 5:
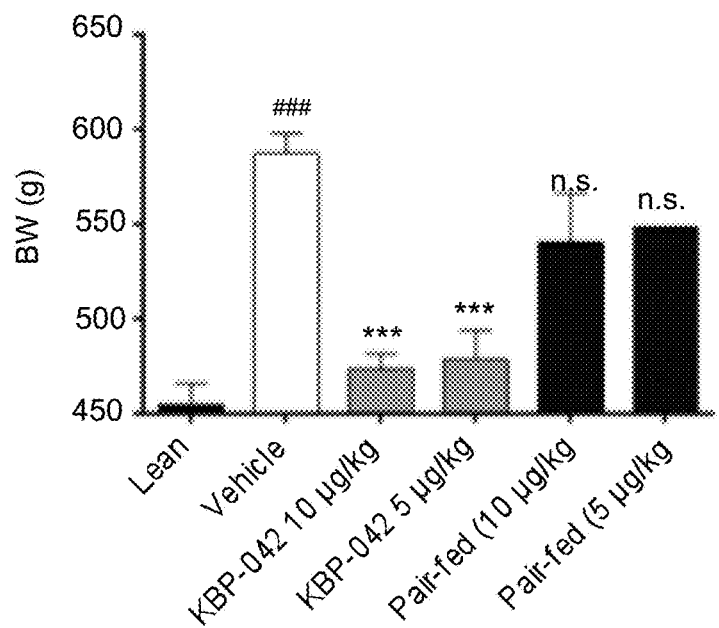

FIG. 5 shows absolute bodyweight at termination of the study. Lean represents a non-obese control group, and the vehicle is the obese control group. The pair-fed groups to the right illustrate groups where the food of the control group has been restricted to match the level of the corresponding active treatment group, and thereby shows the weight loss introduced specifically by the reduction in food intake.

Figure 6:
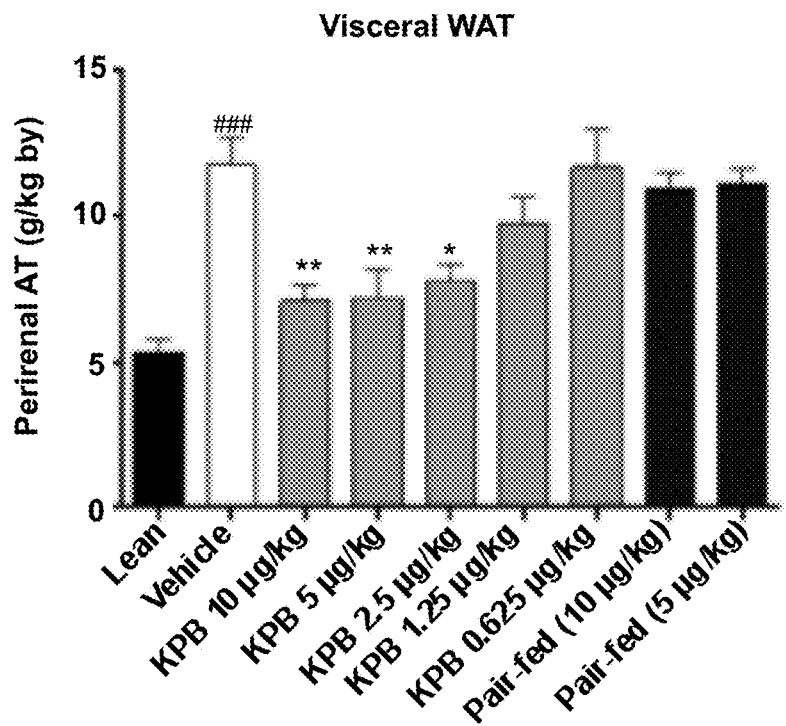

FIG. 6 shows measurement of the weight of the perirenal fat depot at termination.

Figure 7:
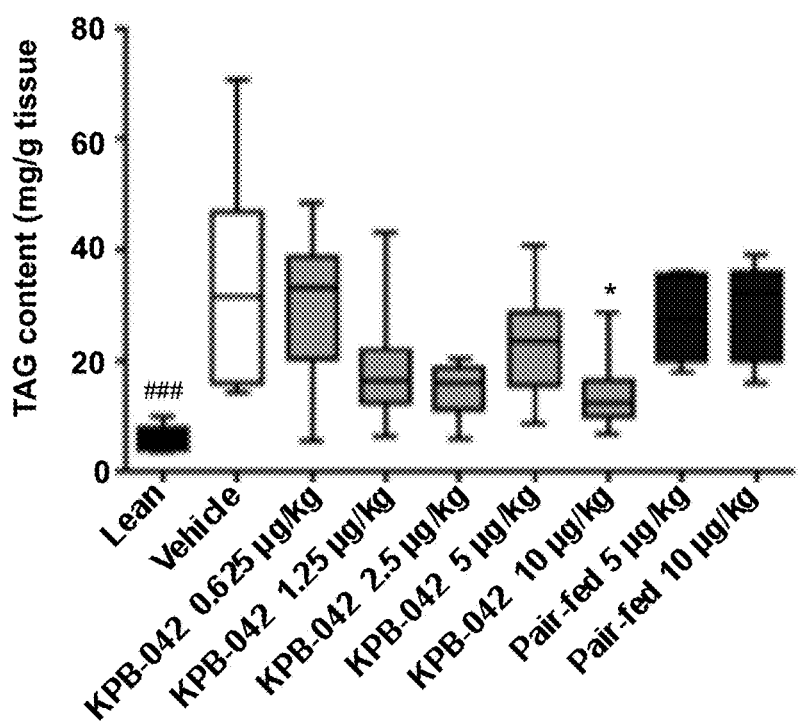

FIG. 7 shows results of extraction of triacylglycerols from the liver collected at termination of the experiment.

FIG. 8 shows the results of body weight reduction using KBP-042.

FIG. 9 summarises all of the results from the tests performed in Example 2.

FIG. 10 shows the results of Adipose Tissue reduction using KBP-042.

FIG. 11 shows Oil red O staining of frozen liver sections (magnification ×40): (A) Lean; (B) Vehicle; (C) 2.5 µg/kg KBP-042; (D) 2.5 µg/kg KBP-089; (E) Pair-fed KBP-089; (F) Quantification.

FIG. 12 shows blood glucose and insulin levels during oral glucose tolerance test (OGTT) performed in animals treated with KBP-042 or vehicle.

FIG. 13 shows the effect of KBP-042 on insulin sensitivity.

EXAMPLE 1

Two studies were conducted, and in both studies the obese rats used were generated as follows:

To obtain obese rats, male Sprague-Dawley rats aged 12 weeks were placed on a diet consisting of regular rodent chow and a 60 kcal % high-fat diet (no. D12495; Research Diets) for a total of 12 wk. Following the 12 weeks on high fat diet the rats were randomized into treatment groups based on weight.

The initial study was a 16-day treatment study, in which three groups were studied: Lean (same age but no high fat diet), vehicle (obese control group), and KBP-042 at 7.5 µg/kg/day. Throughout the experiment the bodyweight and food intake were monitored, and at termination liver and fat depots were collected for weighing and potential analysis of triglyceride, free fatty acids and arachidonic acid content.

The second study consisted of the following groups: vehicle, KBP-042 0.625 µg/kg/day, KBP-042 1.25 µg/kg/day, KBP-042 2.5 µg/kg/day, KBP-042 5 µg/kg/day, KBP-042 10 µg/kg/day, pair-fed (calorie restriction) matching the 5 µg/kg/day and pair-fed (calorie restriction) matching the 10 µg/kg/day, to allow assessment of the effect of KBP-042 on bodyweight independent of its effect on food intake.

Throughout the experiment the bodyweight and food intake were monitored, and at termination liver and fat depots were collected for weighing and potential analysis of triglyceride content.

Tissue Lipid Analysis
Preparation of Internal Standard

As the quantification procedure contains several steps an internal standard was added to each sample extraction, which enables the results to be normalized and correcting for any loss. The internal standard was prepared as a solution containing 3.66 mg/mL C19:0 TAG (Sigma-Aldrich, product number: T4632), 2.73 mg/mL C17:0 Phospholipid (PL), 0.4 mg/mL C19:0 FFA (Sigma-Aldrich, product number: N-8263), 0.096 mg/mL C15:0 Diacylglycerol (DAG), 0.06 mg/mL d31-tagged Ceramide, 0.03 mg/mL d7-tagged Sphingosine, 1.036 mg/mL Sitostanol, 0.04 mg/mL d31-tagged Sphingomyelin and 1.596 mg/mL C15:0 Cholesterolester in Chloroform:Methanol 2:1 (v/v).

Tissue Lipid Extraction

The method is based on Folch et al [89][90, 91]. At the time of extraction the samples were portioned at 500 mg individually and transferred to glass tubes, followed by the addition of 10 mL 100 μg/mL butylated hydroxytoluene (BHT) in chloroform:methanol 2:1 (v:v), and placed on ice. Each sample was added 150 μL of the internal standard solution. Homogenization was performed using a rotor-stator submersion blender (IKA Ultra-Turrax T25) with the sample tubes submerged in ice-water. The samples were each homogenized for 3×10 seconds with 50 second intervals, where after the homogenate is transferred to 35 mL screw-cap centrifuge tubes. The aggregate was cleaned in 5 mL chloroform:methanol 2:1 in the original glass tube, which was then transferred quantitatively to the homogenate. The homogenate was added 3 mL (0.24 times the total homogenate volume) of 0.73% (w/v) NaCl in MiliQ H2O and mixed, followed by centrifugation at 2800·g for 5 minutes at 4° C., to create a 2-phase system. The lower phase was transferred to a clean 12.5 mL centrifugation tube. The homogenate (the upper phase) was then added 3 mL chloroform:methanol 85:15 and mixed, followed by another centrifugation step. The new lower phase was then isolated and added to the first extract and dried down under nitrogen in a 40° C. water bath, followed by resolubilization in 300 μL chloroform:methanol 2:1. At this point the lipid extracts can be stored at −20° C.

Lipid Fractionation

The lipid extracts were fractionated on amino-propyl columns (Phenomenex Strata NH2, product number: 8B-S009-HBJ). The columns were pre-washed with 2×2 mL chloroform:methanol 23:1 (v:v) and left to dry. During fractionation the columns were not allowed to dry. The columns were primed with 2×1 mL hexane followed by application of the lipid extracts. Fraction 1 containing cholesterol esters was eluted with 3 mL Hexane into a clean tube. Fraction 2 containing TAG was eluted using 3 mL hexane:chloroform:ethylacetate 100:5:5 (v:v:v) into a clean tube. Fraction 3 containing DAG, Cholesterol and Ceramide was eluted using 3×2 mL chloroform:methanol 23:1 (v:v) into a new glass. Fraction 4 containing FFA was eluted using 5 mL 2% acetic acid in diethyl ether into a new glass. Fraction 5 containing PL was eluted using 4 mL methanol into a new glass. Fractions 1 and 2 were dried down under nitrogen at 40° C. and re-dissolved in 300 μL chloroform:methanol 95:5 and stored at −20° C. Fraction 4 and half of fraction 5 (fraction 5A) were dried down under nitrogen at 40° C. and re-dissolved in 300 μL chloroform:methanol 2:1 and stored at −20° C. Fraction 3 was equally dried down and re-dissolved in 135 μL chloroform and 67.5 μL isopropanol, transferred to HPLC vials and stored at −20° C. The other half of fraction (fraction 5B) was dried down under nitrogen and re-dissolved in 200 μL chloroform:isopropanol 1:1 (v:v), transferred to HPLC vials and stored at −20° C.

Fatty Acid Methylation

To allow gas chromatographic analysis of the fatty acids they must be converted to the more volatile Fatty Acid Methyl Ester (FAME) form. This is performed using a boron trifluoride catalyzed methylation in methanol. For the methylation step triacylglycerols must be hydrolysed, which is performed under alkaline conditions in the first step of the procedure. This is followed by methylation and extraction of the FAME products. Fractions were dried down under nitrogen at 40° C., followed by the addition of 1 mL of 0.5 M NaOH in methanol. The sample tubes tightly closed with screw caps were allowed to reflux for 5 minutes at 80° C. in a heating block to mediate hydrolysis. After the hydrolysis step the samples were allowed to cool to room temperature before the addition of 1 mL 20% BF in methanol and 0.5 mL 0.1% hydroquinone in methanol. The samples were then allowed to reflux at 80° C. for 2 minutes to mediate the methylation, followed by cooling. 2 mL 0.73% NaCl in Milli-Q was added to the samples followed by mixing for 10 seconds. This increases the polarity of the methanol phase by increasing the content of water. The samples were then added 0.5 mL heptane followed by mixing for 10 seconds, to extract the FAMES, and centrifuged at 2800·g for 1 minute. The top phase (heptane) was transferred to a clean 3 mL centrifuge tube. An additional 0.5 mL heptane was added to the methylated sample, mixed, centrifuged and transferred to the first extract. The remaining solution was discarded. The top phases (heptane extract) were added 1 mL saturated alkaline NaCl solution, mixed for 10 seconds and centrifuged at 2800·g for 1 minute. The top phase was then transferred to a new 3 mL tube. The TAG fraction is ready to use after methylation and were transferred to GC vials with low-volume inserts.

Lipid Analysis Using GC-FID

The methylated lipid fractions were analysed using an Agilent 6890N gas chromatograph with a fused silica capillary column (Sigma-Aldrich; Supelco SP-2380, product number: 24111) and a Flame Ionization Detector (FID).

Data Processing

Total triacylglycerol and arachidonic acid were calculated as the ratio of the total peak area (Areatot) (subtracted the area of the internal standard) to the area of the internal standard Areain-std), multiplied by the mass of the internal standard(min-std). This is detailed in equation (1). To achieve the final concentration, the total content was normalised by sample weight.

$$\text{Total Content} = \frac{(Area_{tot} - Area_{in\text{-}std})}{Area_{in\text{-}std}} \cdot m_{in\text{-}std} \qquad \text{Equation (1)}$$

The content of individual fatty acids were identified and calculated as the ratio of the individual fatty acid peak area (AreaF A) to total identified fatty acid area (AreaID) subtracted the peak area of the internal standard (Areain-std) and expressed in percent. This is detailed in equation (2).

$$\text{Area } \%_{FA} = \frac{Area_{FA}}{Area_{ID} - Area_{in\text{-}std}} \cdot 100 \qquad \text{Equation (2)}$$

Results

Figure 1A:
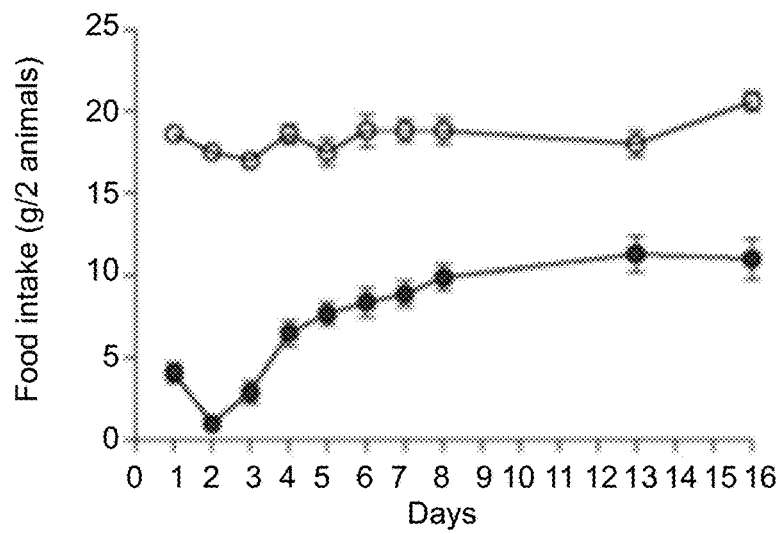
FIG. 1 shows food intake, bodyweight and weight of the epididymal adipose tissue depot at termination in a 16-day study.
Figure 1B:
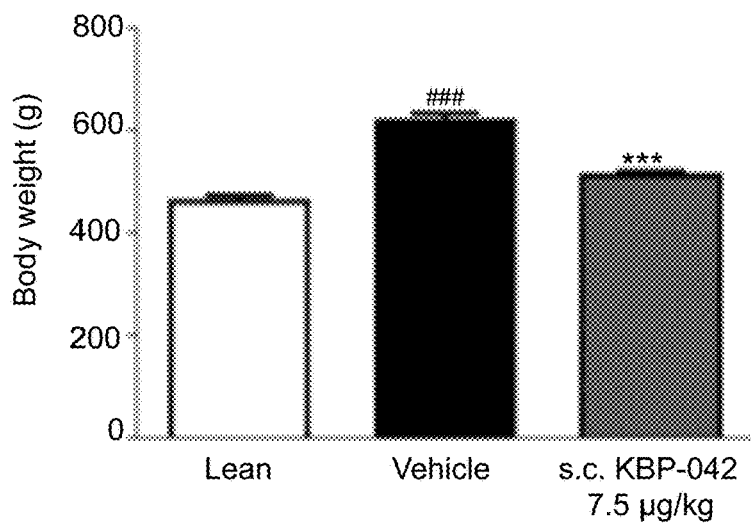
Figure 1C:
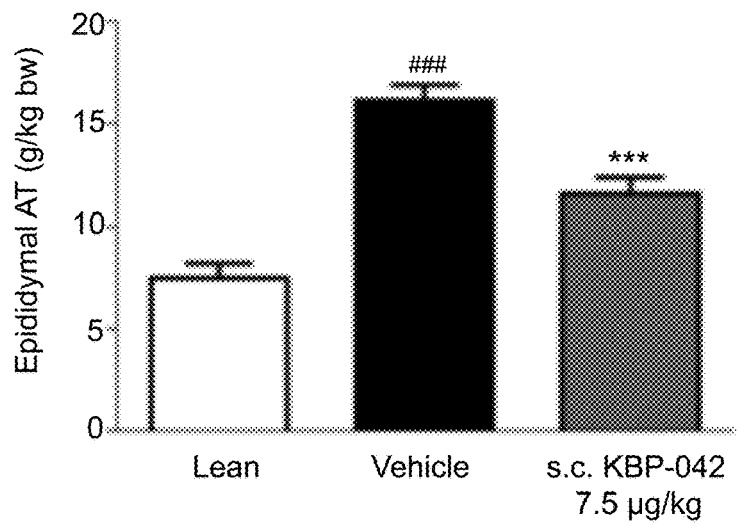

Results of the 16 day initial study are shown in FIGS. 1-3. As seen in FIG. 1, the peptide AcCSNLSTCVLGKLSQEL-HKLQTYPRTDVGANAP-NH$_2$ (KBP-042) (SEQ ID NO: 54) reduced food intake (A) body weight gain (B) and visceral fat (epididymal) (C) within 16-days of treatment when compared to saline.

As seen in FIGS. 2A-2B, the KBP-peptide produced an improvement in triacylglycerols and arachidonic acid (a pro-inflammatory mediator) content in extracted liver tissue.

As seen in FIG. 3, the KBP-peptide produced an improvement in Free Fatty Acids content in extracted liver tissue.

The 16-day study thus demonstrated that KBP-042 as expected produced a pronounced reduction in food intake early, which led to a marked weight reduction. Furthermore, fats depots were reduced. Importantly, analysis of the liver fatty acid composition showed that KBP-042 reduced triacylglycerols and free fatty acid accumulation, indicating a benefit on fatty liver. Finally, KBP-042 reduced the levels of the fatty acid arachidonic acid in the liver, and arachidonic acid is a known pro-inflammatory mediator, and therefore reduction of the levels of this molecule should be beneficial in terms of preventing fatty liver and steatosis in the liver.

The results of the 8-week study are seen in FIGS. 4-7, confirmed all of these initial study findings.

Figure 4:
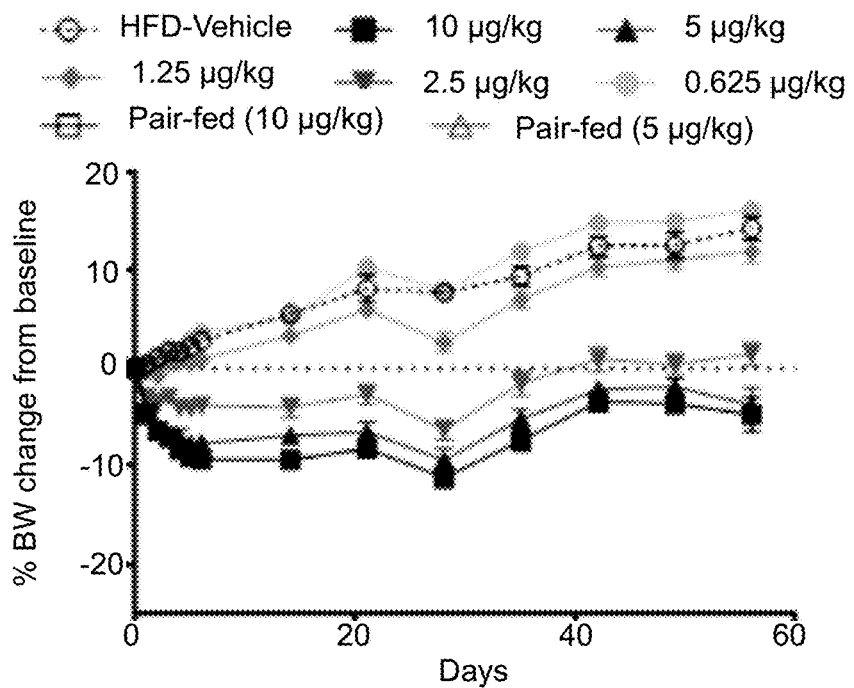
FIG. 4 shows bodyweight as a function of treatment over 60 days presented as baseline normalized bodyweight as a function of time in five dose groups and a vehicle arm.

As seen in FIG. 4, the KBP-peptide produced a marked weight reduction even when compared to the calorie restricted groups (pair-fed), showing a substantial weight loss independent of the regulation of food intake. The 8-week study also included a pair-fed control (calorie restriction), and as such also confirmed the beneficial effects of KBP-042 on bodyweight and fatty liver independent of the reduction in food intake.

As seen in FIG. 5, the KBP peptide reduced perirenal fat depot measurements compared to vehicle, even in a pair fed experiment.

As seen in FIG. 6, the KBP peptide reduced triglyceride content of the liver compared to vehicle, even in a pair fed experiment.

As seen in FIG. 7, the KBP-peptide produced an improvement in triacylglycerols after 8 weeks of treatment.

EXAMPLE 2

Body Weight Reduction (KBP-042)

A normal diet group (ND) was included as a reference for all parameters studied in high fat diet (HFD) rats. Endpoint data from the ND group appear in FIG. 8 and all results from the performed tests are summarized in FIG. 9 and are compared to HFD-Vehicle.

FIG. 8 shows: A) Absolute body weight progression during the study from randomization at day 0 to last day of treatment, day 56; B) Vehicle-corrected body weights; C) Endpoint body weights; D) Food intake of all treatment groups during the entire study. Food intake was monitored every day for the first 6 days followed by weekly monitoring. Pair-fed groups were fed the same as the average for their corresponding treatment group (5 µg/kg or 10 µg/kg). n=10 for all groups except vehicle (n=12). Statistical analysis between groups for C), E) and F) were performed as a One-way ANOVA followed by Tukey's post-hoc test with the following annotations: ###P<0.001 vs. ND-control *P<0.05, P<0.01, *P<0.001 vs. HFD-Vehicle, ††P<0.01, †††P<0.001 vs. Pair-fed 5 µg/kg, ‡‡P<0.01, ‡‡‡P<0.001 vs. Pair-fed 10 µg/kg, Data are expressed as mean±SEM.

In general the HFD-Vehicles had impaired glucose tolerance (higher total area under the curve) in the oral and intravenous glucose tolerance tests, with higher insulin levels in both tests. All data showing that HFD rats were obese and pre-diabetic at the initiation of treatment were as expected.

Figure 8C:
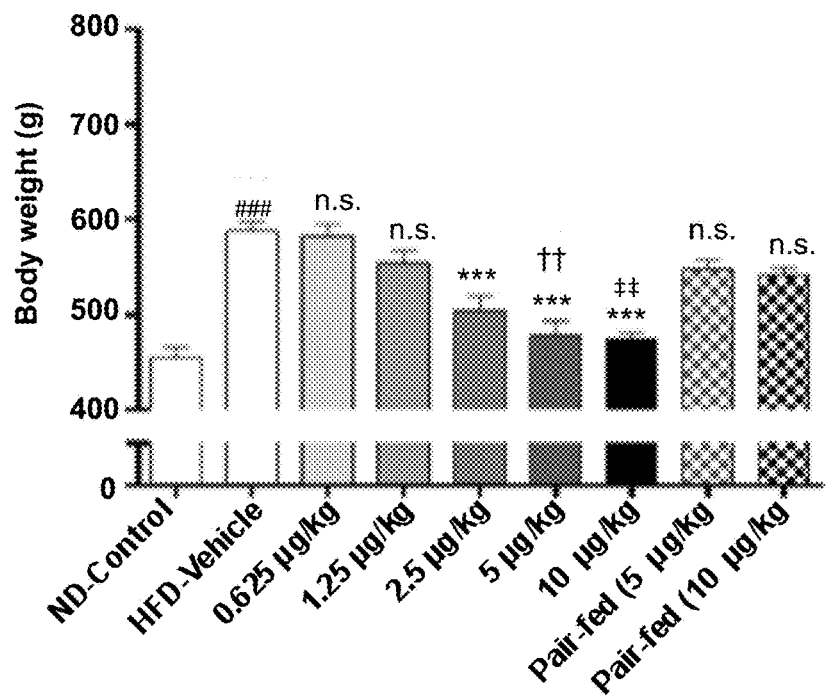
Figure 8D:
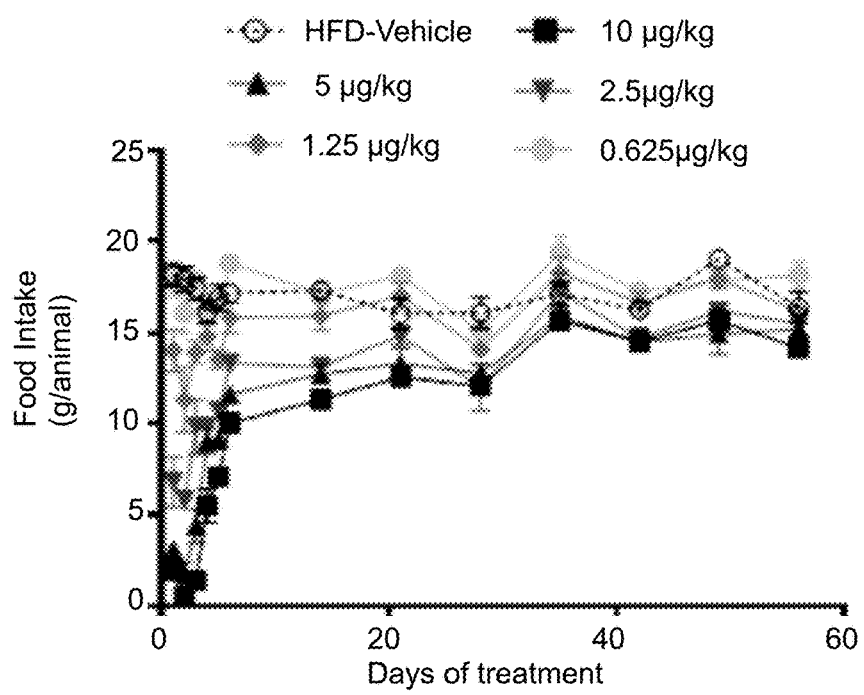
Figure 8E:
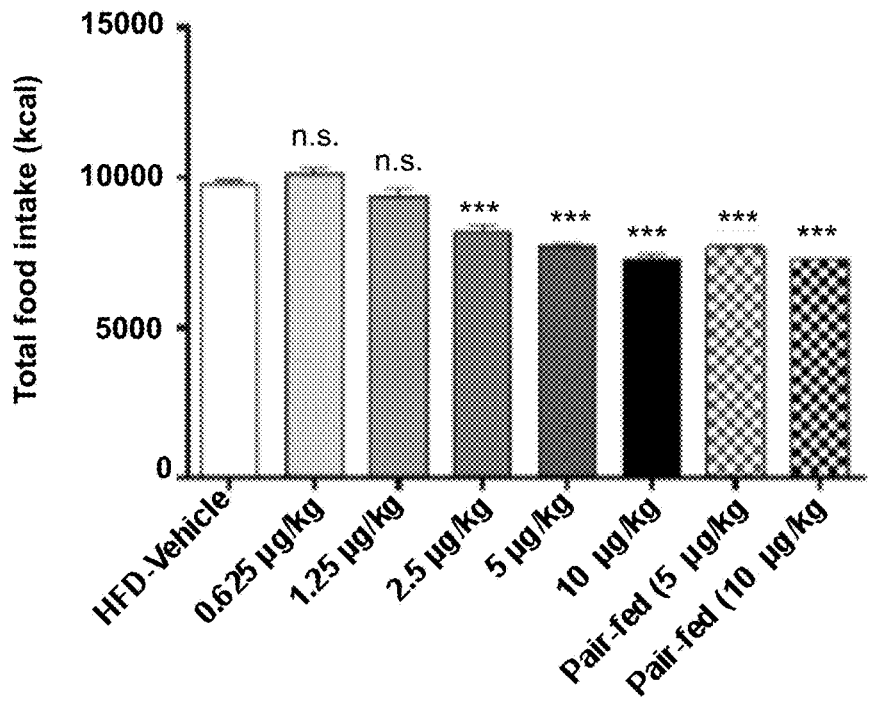
Figure 8F:
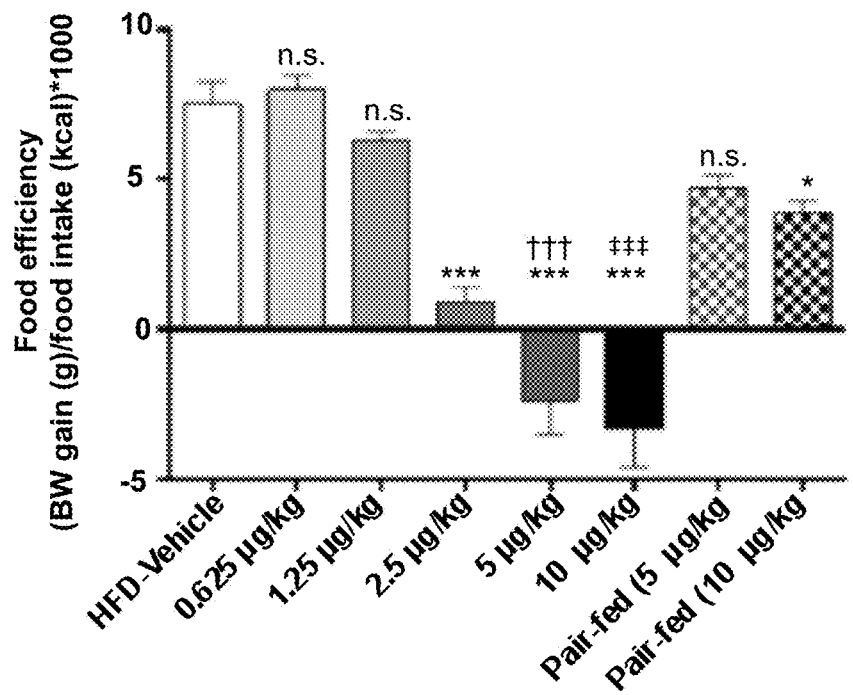

After treatment with KBP-042 for 8 weeks, there was a dose-dependent and sustained reduction of body weight. A large weight loss was observed in the initial phase of the study (FIGS. 8A and 8B) in the three highest treatment groups (2.5 µg/kg, 5 µg/kg and 10 µg/kg), as well as the two corresponding pair-fed groups (Pair-fed 5 µg/kg and Pair-fed 10 µg/kg). This corresponds well with the large reduction in food intake in the first 6 days of treatment (FIG. 8D). However, after this transient large reduction in feeding, food intake normalised during the course of the study. The pair-fed groups gained weight again after food intake increased, whereas the KBP-042 treatment sustained the initial weight reduction throughout the 56 days of treatment. At day 56 animals were weighed and treatment with KBP-042 was evaluated. Body weight was significantly lower for the 2.5 µg/kg, 5 µg/kg and 10 µg/kg groups compared to the HFD-vehicle. The reduced food intake corresponds well with the body weight change for the three highest treatment groups (2.5 µg/kg, 5 µg/kg and 10 µg/kg) (FIG. 8E), although the pair-fed groups which received the same amount of food as their corresponding treatment-group, did not have significantly different weight than the HFD-vehicle animals.

On the basis of food intake and body weight change the food efficiency was calculated (FIG. 8F), and as expected KBP-042 treatment with 2.5 µg/kg, 5 µg/kg and 10 µg/kg resulted in a drastic reduction in food efficiency, which was significantly different from the pair-fed controls, possibly indicating increased energy expenditure.

In conclusion, KBP-042 mediated a large reduction in body weight and maintained weight loss for 8 weeks.

EXAMPLE 3

Reduction In Adipose Tissue (KBP-042)

At the end of the study of Example 2 three different adipose tissues were isolated.

The results are shown in FIG. 10: A)-C) Weight of isolated epididymal, inguinal and perirenal white adipose tissue respectively after 56 days of treatment; D) Total triacylglyceride content extracted from liver tissue after treatment with KBP-042 or saline for 56 days; E),F) Plasma Adiponectin and Leptin levels respectively after 56 days of treatment. n=10 for all groups except vehicle (n=12). Statistical analysis between groups were performed as a One-way ANOVA followed by Tukey's post-hoc test with the following annotations: ##P<0.01, ###P<0.001 vs. ND-control. *P<0.05, P<0.01, *P<0.001 vs. HFD-Vehicle. †P<0.05, ††P<0.01 vs. Pair-fed 5 µg/kg. ‡P<0.05 vs. Pair-fed 10 µg/kg, Data are expressed as mean±SEM As seen in FIGS. 10A-C, the weights of isolated epididymal and perirenal white adipose tissues were significantly reduced after treatment with 10 µg/kg of KBP-042. For the perirenal adipose tissue even the 2.5, 5 and 10 µg/kg groups showed a significant reduction in size. The same reduction was not seen in the pair-fed controls. There was a trend towards reducing inguinal white adipose tissue.

Figure 10A:
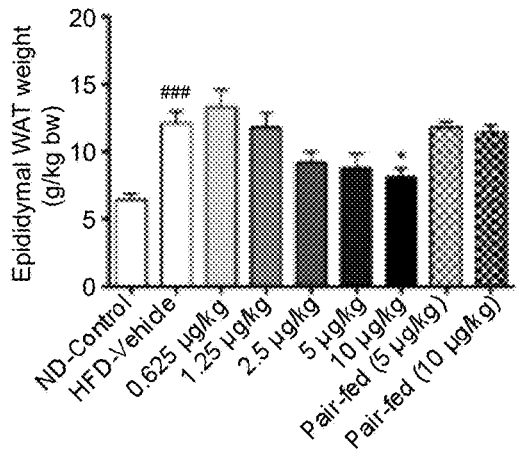
Figure 10B:
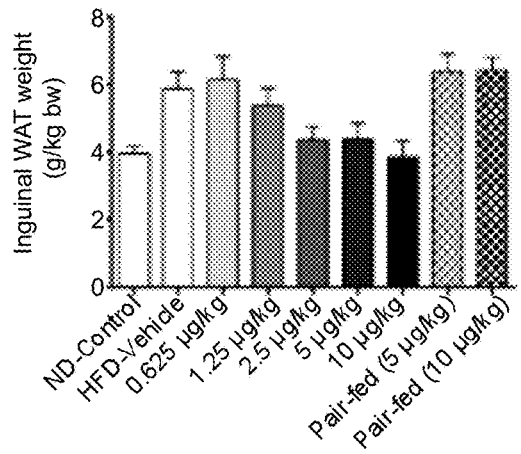
Figure 10C:
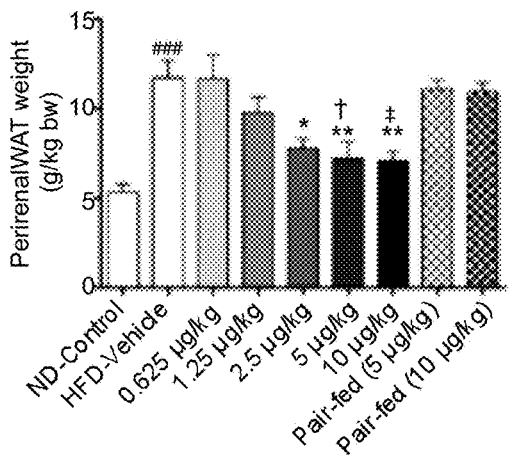
Figure 10D:
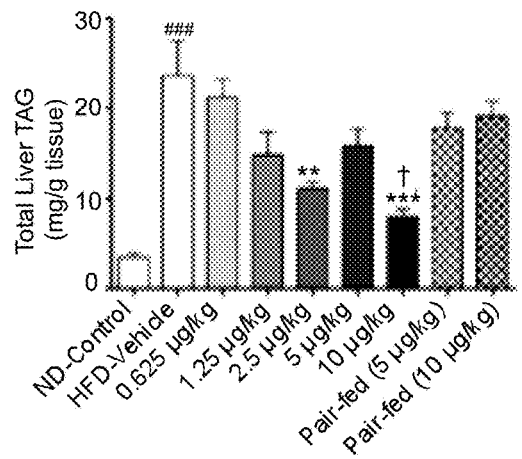

To assess lipid accumulation in liver, triacylglycerols (TAG) were extracted from the liver and analyzed (FIG. 10D). The HFD-Vehicle group had dramatically higher TAG levels compared to ND group, as expected. This accumulation was significantly reduced after treatment with 10 µg/kg KBP-042, while the corresponding pair-fed control group did not show a significant reduction in liver TAG. The large variances in the TAG levels make it difficult to achieve statistical significance however the trends indicated a dose-dependent effect. In order to assess whether the treatment altered fatty acid metabolism in selective ways (e.g. metabolism of saturated vs. monounsaturated vs. polyunsaturated), we also analysed the fatty acid composition of hepatic TAG. The results show that there were no differences in the relative distribution, i.e. the treatment caused a general reduction in TAG without effects on metabolism of specific fatty acid types (FIG. 9).

Figure 10E:
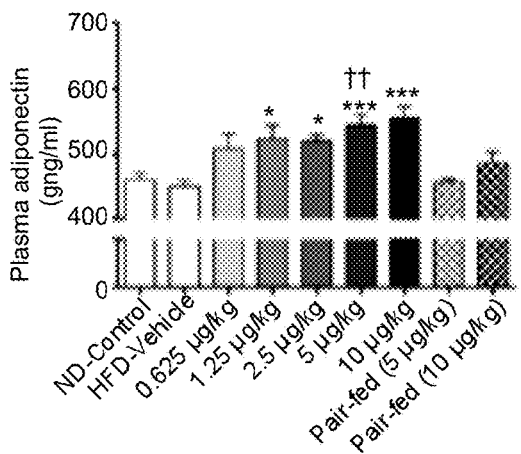
Figure 10F:
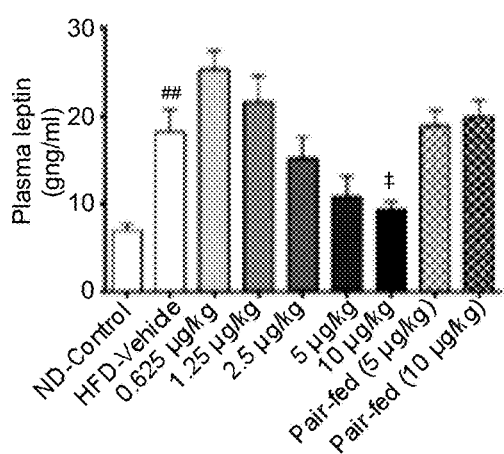

Finally, the two adipokines adiponectin and leptin were measured after 56 days of treatment (FIGS. 10E and 10F).

Adiponectin levels were significantly increased in response to treatment with doses of 1.25 µg/kg, 2.5 µg/kg, 5 µg/kg and 10 µg/kg KBP-042. With respect to leptin, there was trend towards reduced levels of plasma leptin, which reached statistical significance when comparing 10 µg/kg KBP-042 to the corresponding pair-fed control.

In summary, fat depots, lipid, and adipokine data support a strongly improved metabolic status as a function of KBP-042 therapy. Adipose tissues and ectopic lipid accumulation were reduced by KBP-042

EXAMPLE 4

Reduced Levels Of Liver Fat (KBP-042 AND KBP-089)

At termination of the study of Example 2 the rat livers were embedded using snap freezing in OCT, and then sectioned using a cryomicrotome. Sections were prepared from four groups, KBP-042 in HFD rats, KBP-089 in HFD rats, control HFD rats, and a lean rat comparison.

Figure 11A:
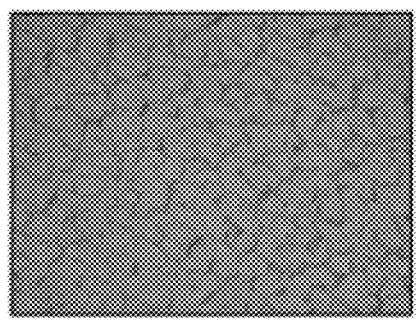
Figure 11B:
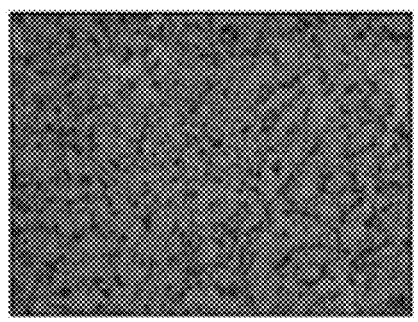

The sections were stained using Oil-Red-O staining. Staining of liver sections from HFD-fed rats (FIG. 11B) showed a significant 57.1% increase (p<0.01) in lipid accumulation compared to lean rats (FIG. 11A). Lipid accumulation in liver from rats daily treated with 2.5 µg/kg KBP-042 (FIG. 11C) decreased HFD-induced lipid accumulation significant with 78.3% (p<0.05) compared to vehicle and was similar to lean rats (p=0.8173). Lipid accumulation in liver from rats treated with 2.5 µg/kg KBP-089 (FIG. 11D) reduced lipid accumulation significant by 155.3% (p<0.001) compared to vehicle and was furthermore similar to lean rats (p=0.9976). The lipid accumulation in pair-fed KBP-089 liver exceeded KBP-089 treated rats with 66.5% (p<0.001) and was not significant different from vehicle (0.6711). Statistical test performed was one-way ANOVA with Dunnet's post test for multiple comparisons. p<0.01, *p<0.001.

Figure 11C:
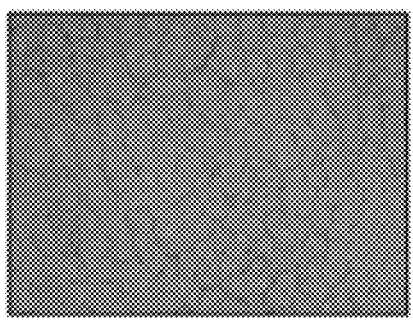
Figure 11D:
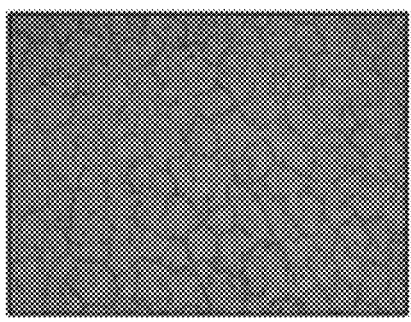
Figure 11E:
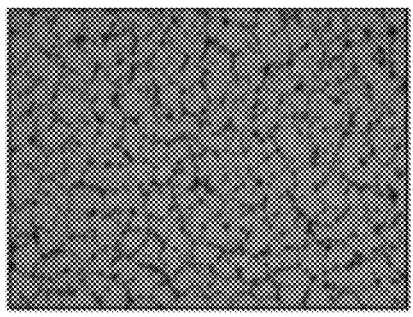
Figure 11F:
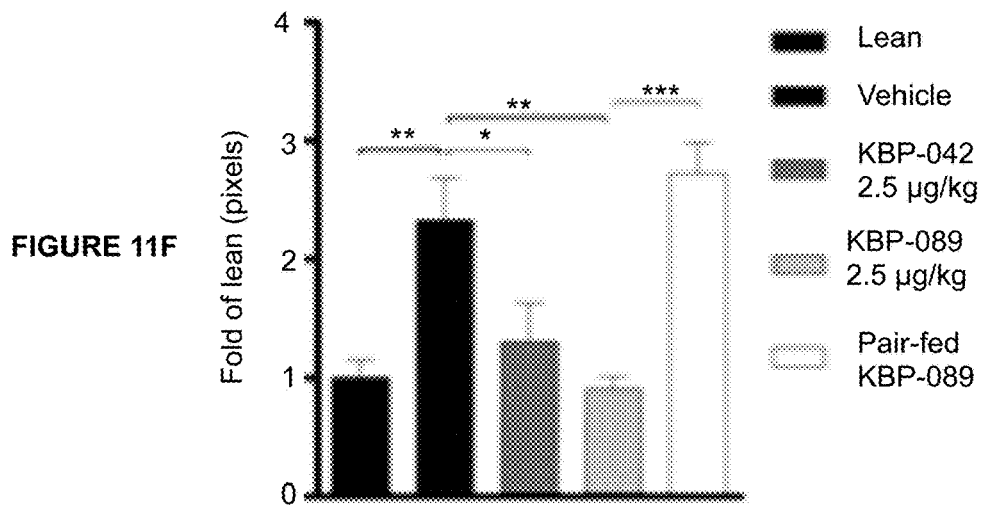

Thus, as seen in FIGS. 11C and 11D, KBP-042 and KBP-089 treatment led to a substantial reduction in lipids present in the liver sections all the way down to the level observed in the lean rats. When quantifying the intensity of the staining (FIG. 11F), these data confirmed that KBP-042 and KBP-089 induced a significant reduction of liver lipid accumulation.

The results indicate that HFD-induced lipid accumulation in liver tissue can be decreased by KBP-treatment but not by calorie restriction.

EXAMPLE 5

Improved Glucose Tolerance (KBP-042)

To assess whether the weight and liver fat reductions manifested in improved glucose tolerance, an oral glucose tolerance test was performed both in treatment naive animals (after a single injection), following 3 weeks and again after 7 weeks of treatment.

Figure 12A:
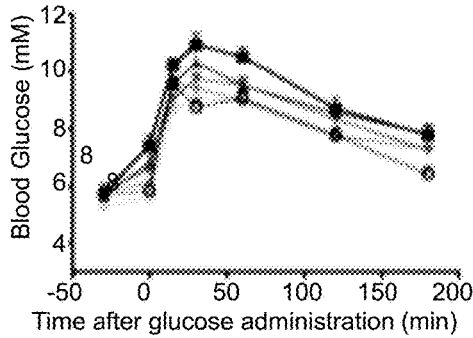
Figure 12D:
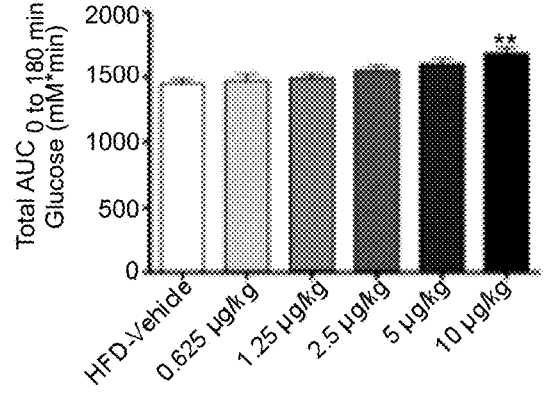
Figure 12B:
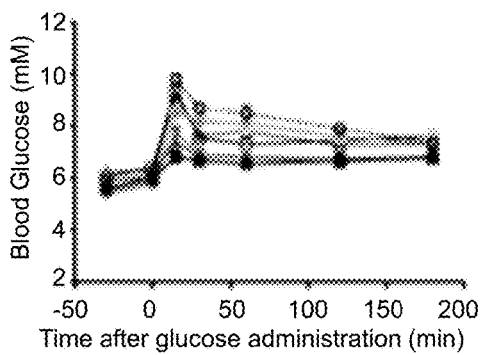
Figure 12E:
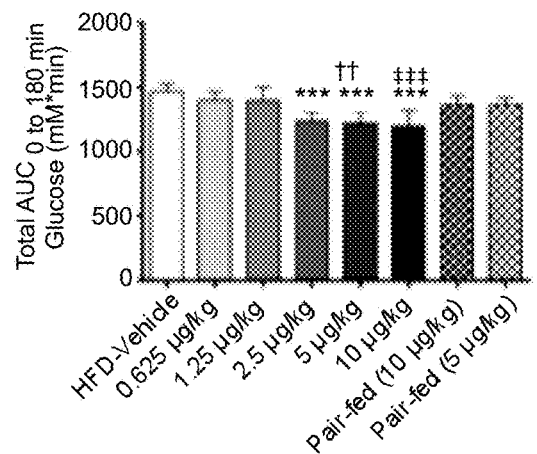
Figure 12C:
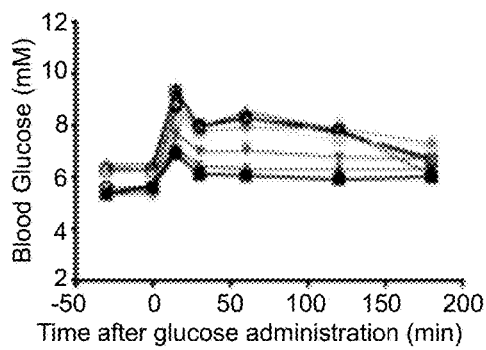
Figure 12F:
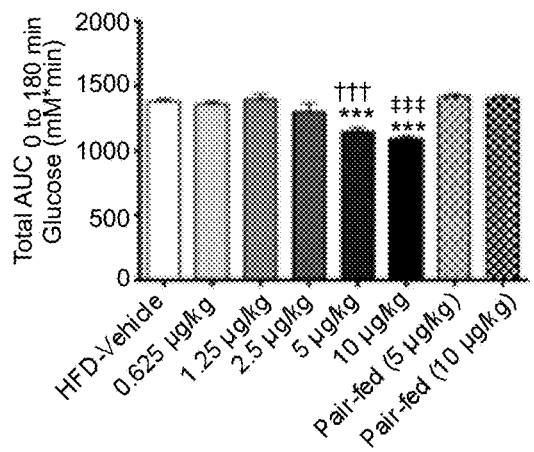
Figure 12G:
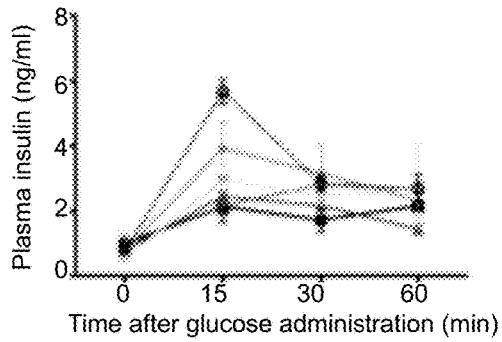
Figure 12J:
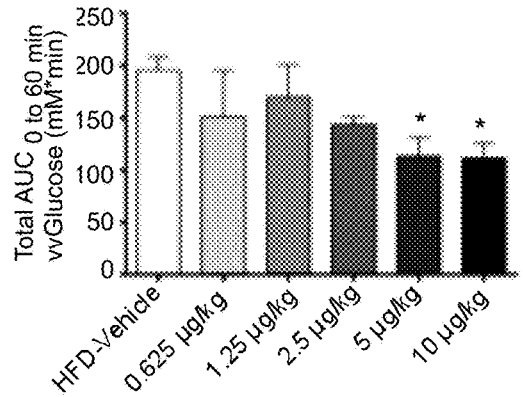
Figure 12H:
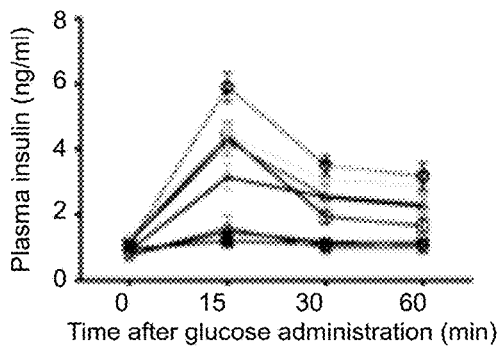
Figure 12K:
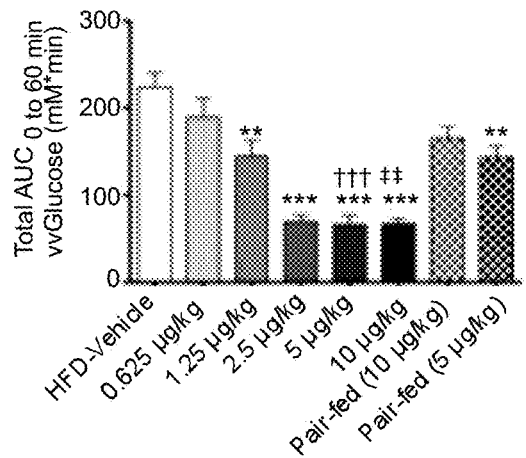
Figure 12I:
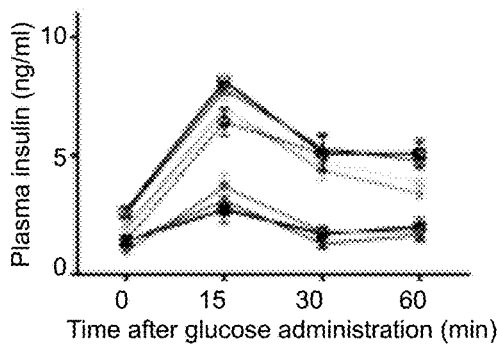
Figure 12L:
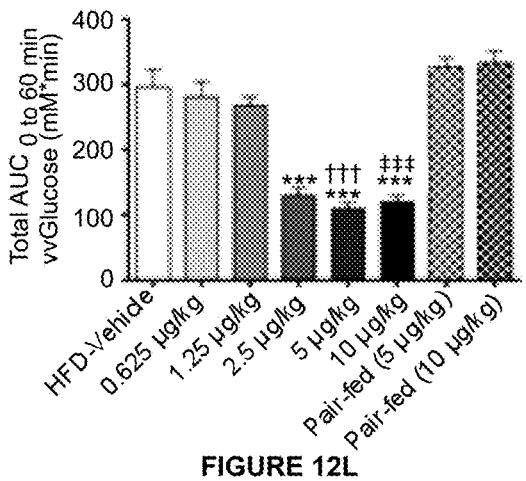

Animals were challenged with an oral glucose bolus (2 g/kg) at time=0, and dosed with either KBP-042 or saline at t=−30. FIGS. 12A, 12B and 12C show blood glucose levels during acute OGTT, OGTT after 3 weeks, and OGTT after 7 weeks respectively. FIGS. 12D, 12E and 12F show the area under the curve for acute OGTT, OGTT after 3 weeks, and OGTT after 7 weeks respectively. FIGS. 12G, 12H and 12I show insulin levels during acute OGTT, OGTT after 3 weeks, and OGTT after 7 weeks respectively. FIGS. 12J, 12K and 12L show insulin levels during acute OGTT, OGTT after 3 weeks, and OGTT after 7 weeks respectively expressed as area under the curve. n=10 for all groups except vehicle (n=12). Statistical analysis between groups were performed as a One-way ANOVA followed by Tukey's post-hoc test with the following annotations: *P<0.05, P<0.01, *P<0.001 vs. HFD-Vehicle. ††P<0.01, †††P<0.001 vs. Pair-fed 5 µg/kg. ‡‡P<0.01, ‡‡‡P<0.001 vs. Pair-fed 10 µg/kg, Data are expressed as mean±SEM.

The OGTT performed after an acute dose showed a slightly impaired glucose tolerance for the 10 µg/kg group compared to HFD-Vehicle (FIG. 12A). A hyperglycemic effect was observed 30 minutes after the subcutaneous administration of KBP-042 (at t=0). The total area under the curve (tAUC) was significantly increased with injection of 10 µg/kg KBP-042 (FIG. 12D). However, the insulin levels during the first 60 minutes after glucose administration were reduced in animals dosed with KBP-042 (FIGS. 12G and 12J).

After 3 weeks of treatment with KBP-042 or saline the three highest doses of KBP-042 (2.5 µg/kg, 5 µg/kg and 10 µg/kg) resulted in a significantly lowered tAUC (FIGS. 12B and 12E). Interestingly, the insulin levels were lowered for all treatment groups except the 0.625 µg/kg KBP-042 group (FIGS. 12H and 12K). The pair-fed 10 µg/kg group also had a reduced insulin response (FIG. 12K).

When the OGTT was performed at week 7 of treatment (FIG. 12C) only the two highest dose groups (5 µg/kg and 10 µg/kg) showed improved glucose tolerance when tAUC was considered (FIG. 12F). Interestingly, the three highest dose groups had increased glucose tolerance (or maintained for the 2.5 µg/kg group), while drastically reduced insulin levels were observed within the first 60 minutes after glucose administration (FIGS. 12I and 12L). No changes in glucose tolerance or insulin levels were observed in the pair-fed groups compared to HFD-Vehicle.

In conclusion, treatment with KBP-042 improved glucose tolerance with reduced insulin levels after chronic treatment

EXAMPLE 6

Effect Of KBP-042 On Insulin Sensitivity

As liver fat is known to decrease insulin sensitivity, the effect of KBP-042 on insulin sensitivity was considered using the glucose infusion rate (GIR) in the hyperinsulinemic-euglycemic clamp. For this study ND rats were compared to insulin resistant HFD rats and 5 µg/kg KBP-042 treated HFD rats.

The results are shown in FIG. 13: A) Glucose infusion rate (GIR) at steady state during hyperinsulinemic-euglycemic clamp when blood glucose was clamped at basal levels after 21 days treatment; B) Body weight at hyperinsulinemic-euglycemic clamp experiment day after 21 days of treatment. Statistical analysis between groups was performed as a One-way ANOVA followed by Tukey's post-hoc test with the following annotations: *P<0.05, P<0.01, *P<0.001. Data are expressed as mean±SEM.

Figure 13A:
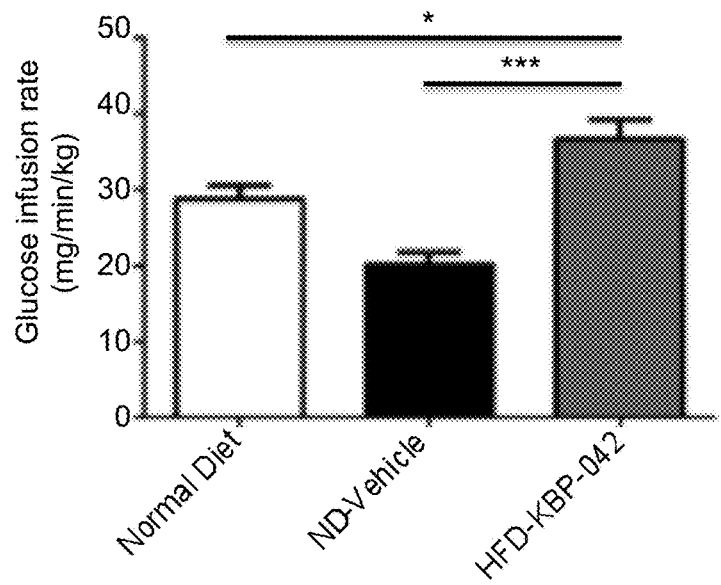
Figure 13B:
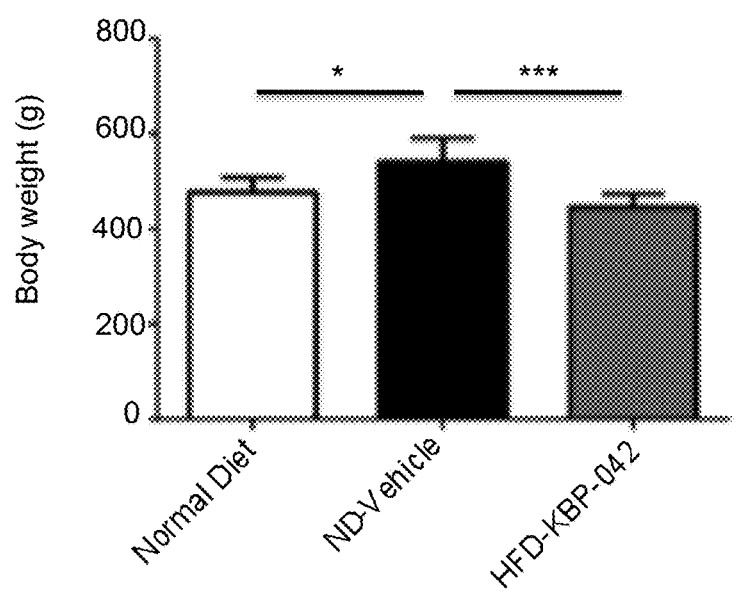

FIG. 13A shows GIR reduced by ~30% (p=0.057) in the HFD group compared to ND. The treatment with KBP-042 led to a significant increase in GIR (82%, p<0.001) compared to HFD-Vehicle. When KBP-042 treatment is compared to ND GIR is increased with 27% (p<0.05). As expected the body weight was increased after HFD for 10 weeks as compared to ND (FIG. 13B). FIG. 13B shows that the treatment with KBP-042 for 21 days reduced the body weight by ~18% and the body weight was not significantly different from the ND rats at the end of the study.

Thus, KBP-042 improved whole-body insulin sensitivity in the hyperinsulinemic-euglycemic clamp In summary, we here present a novel possibility for reduction of fatty liver, a disease which has become prominent within the last decades due to the increasing occurrence of obesity.

In this specification, unless expressly otherwise indicated, the word 'or' is used in the sense of an operator that returns a true value when either or both of the stated conditions is met, as opposed to the operator 'exclusive or' which requires that only one of the conditions is met. The word 'comprising' is used in the sense of 'including' rather than in to mean 'consisting of'. All prior teachings acknowledged above are hereby incorporated by reference. No acknowledgement of any prior published document herein should be taken to be an admission or representation that the teaching thereof was common general knowledge in Australia or elsewhere at the date hereof.

The invention claimed is:

1. A method of producing a decrease in liver triglycerides or reducing fat accumulation or a combination thereof in the liver of a subject mammal in need thereof which comprises administering an effective amount of a calcitonin analogue comprising a sequence shown in SEQ ID NO: 31.

2. The method as claimed in claim 1, wherein the amount administered is from 0.001 to 50 µg/kg/day.

3. The method as claimed in claim 1, wherein the amount administered is from 0.01 to 5 µg/kg/day.

4. The method as claimed in claim 1, wherein the subject is a human.

5. The method as claimed in claim 1, wherein the calcitonin analogue sequence comprises SEQ ID NO: 58.

* * * * *

```
                        SEQUENCE LISTING

<160> NUMBER OF SEQ ID NOS: 74

<210> SEQ ID NO 1
<211> LENGTH: 32
<212> TYPE: PRT
<213> ORGANISM: Artificial Sequence
<220> FEATURE:
<223> OTHER INFORMATION: General Formula
<220> FEATURE:
<221> NAME/KEY: SITE
<222> LOCATION: 2
<223> OTHER INFORMATION: A or S
<220> FEATURE:
<221> NAME/KEY: SITE
<222> LOCATION: 8
<223> OTHER INFORMATION: V or M
<220> FEATURE:
<221> NAME/KEY: SITE
<222> LOCATION: 11
<223> OTHER INFORMATION: K or R
<220> FEATURE:
<221> NAME/KEY: SITE
<222> LOCATION: 13
<223> OTHER INFORMATION: S or T
<220> FEATURE:
<221> NAME/KEY: SITE
<222> LOCATION: 15
<223> OTHER INFORMATION: D or E
<220> FEATURE:
<221> NAME/KEY: SITE
<222> LOCATION: 18
<223> OTHER INFORMATION: K or R
<220> FEATURE:
<221> NAME/KEY: SITE
<222> LOCATION: 21
<223> OTHER INFORMATION: T or S
<220> FEATURE:
<221> NAME/KEY: SITE
<222> LOCATION: 22
<223> OTHER INFORMATION: F or Y
<220> FEATURE:
<221> NAME/KEY: SITE
<222> LOCATION: 24
<223> OTHER INFORMATION: K or R
<220> FEATURE:
<221> NAME/KEY: SITE
<222> LOCATION: 29
<223> OTHER INFORMATION: A or S
<220> FEATURE:
<221> NAME/KEY: SITE
<222> LOCATION: 32
<223> OTHER INFORMATION: P or Y

<400> SEQUENCE: 1

Cys Xaa Ser Leu Ser Thr Cys Xaa Leu Gly Xaa Leu Xaa Gln Xaa Leu
1               5                   10                  15

His Xaa Leu Gln Xaa Xaa Pro Xaa Thr Asp Val Gly Xaa Asn Ala Xaa
            20                  25                  30

<210> SEQ ID NO 2
<211> LENGTH: 32
<212> TYPE: PRT
<213> ORGANISM: Artificial Sequence
<220> FEATURE:
<223> OTHER INFORMATION: General Formula
```

```
<220> FEATURE:
<221> NAME/KEY: SITE
<222> LOCATION: 8
<223> OTHER INFORMATION: V or M
<220> FEATURE:
<221> NAME/KEY: SITE
<222> LOCATION: 11
<223> OTHER INFORMATION: K or R
<220> FEATURE:
<221> NAME/KEY: SITE
<222> LOCATION: 15
<223> OTHER INFORMATION: D or E
<220> FEATURE:
<221> NAME/KEY: SITE
<222> LOCATION: 18
<223> OTHER INFORMATION: K or R
<220> FEATURE:
<221> NAME/KEY: SITE
<222> LOCATION: 21
<223> OTHER INFORMATION: T or S
<220> FEATURE:
<221> NAME/KEY: SITE
<222> LOCATION: 22
<223> OTHER INFORMATION: F or Y
<220> FEATURE:
<221> NAME/KEY: SITE
<222> LOCATION: 24
<223> OTHER INFORMATION: K or R
<220> FEATURE:
<221> NAME/KEY: SITE
<222> LOCATION: 29
<223> OTHER INFORMATION: A or S
<220> FEATURE:
<221> NAME/KEY: SITE
<222> LOCATION: 31
<223> OTHER INFORMATION: A or T
<220> FEATURE:
<221> NAME/KEY: SITE
<222> LOCATION: 32
<223> OTHER INFORMATION: P or Y

<400> SEQUENCE: 2

Cys Ser Asn Leu Ser Thr Cys Xaa Leu Gly Xaa Leu Ser Gln Xaa Leu
1               5                   10                  15

His Xaa Leu Gln Xaa Xaa Pro Xaa Thr Asp Val Gly Xaa Asn Xaa Xaa
            20                  25                  30

<210> SEQ ID NO 3
<211> LENGTH: 32
<212> TYPE: PRT
<213> ORGANISM: Artificial Sequence
<220> FEATURE:
<223> OTHER INFORMATION: General Formula
<220> FEATURE:
<221> NAME/KEY: SITE
<222> LOCATION: 8
<223> OTHER INFORMATION: V or M
<220> FEATURE:
<221> NAME/KEY: SITE
<222> LOCATION: 11
<223> OTHER INFORMATION: K or R
<220> FEATURE:
<221> NAME/KEY: SITE
<222> LOCATION: 13
<223> OTHER INFORMATION: S or T
<220> FEATURE:
<221> NAME/KEY: SITE
<222> LOCATION: 15
<223> OTHER INFORMATION: D or E
<220> FEATURE:
<221> NAME/KEY: SITE
<222> LOCATION: 18
<223> OTHER INFORMATION: K or R
```

```
<220> FEATURE:
<221> NAME/KEY: SITE
<222> LOCATION: 21
<223> OTHER INFORMATION: S or T
<220> FEATURE:
<221> NAME/KEY: SITE
<222> LOCATION: 22
<223> OTHER INFORMATION: F or Y
<220> FEATURE:
<221> NAME/KEY: SITE
<222> LOCATION: 24
<223> OTHER INFORMATION: K or R
<220> FEATURE:
<221> NAME/KEY: SITE
<222> LOCATION: 29
<223> OTHER INFORMATION: A or S
<220> FEATURE:
<221> NAME/KEY: SITE
<222> LOCATION: 32
<223> OTHER INFORMATION: P or Y

<400> SEQUENCE: 3

Cys Ala Ser Leu Ser Thr Cys Xaa Leu Gly Xaa Leu Xaa Gln Xaa Leu
1               5                   10                  15

His Xaa Leu Gln Xaa Xaa Pro Xaa Thr Asp Val Gly Xaa Asn Ala Xaa
            20                  25                  30

<210> SEQ ID NO 4
<211> LENGTH: 32
<212> TYPE: PRT
<213> ORGANISM: Artificial Sequence
<220> FEATURE:
<223> OTHER INFORMATION: Synthetic Construct
<220> FEATURE:
<221> NAME/KEY: SITE
<222> LOCATION: 15
<223> OTHER INFORMATION: D or E
<220> FEATURE:
<221> NAME/KEY: SITE
<222> LOCATION: 21
<223> OTHER INFORMATION: S or T
<220> FEATURE:
<221> NAME/KEY: SITE
<222> LOCATION: 22
<223> OTHER INFORMATION: F or Y
<220> FEATURE:
<221> NAME/KEY: SITE
<222> LOCATION: 32
<223> OTHER INFORMATION: P or Y

<400> SEQUENCE: 4

Cys Ala Ser Leu Ser Thr Cys Met Leu Gly Arg Leu Ser Gln Xaa Leu
1               5                   10                  15

His Arg Leu Gln Xaa Xaa Pro Lys Thr Asp Val Gly Ala Asn Ala Xaa
            20                  25                  30

<210> SEQ ID NO 5
<211> LENGTH: 32
<212> TYPE: PRT
<213> ORGANISM: Artificial Sequence
<220> FEATURE:
<223> OTHER INFORMATION: Synthetic Construct
<220> FEATURE:
<221> NAME/KEY: SITE
<222> LOCATION: 11
<223> OTHER INFORMATION: K or R
<220> FEATURE:
<221> NAME/KEY: SITE
<222> LOCATION: 18
<223> OTHER INFORMATION: K or R
```

```
<220> FEATURE:
<221> NAME/KEY: SITE
<222> LOCATION: 22
<223> OTHER INFORMATION: F or Y
<220> FEATURE:
<221> NAME/KEY: SITE
<222> LOCATION: 31
<223> OTHER INFORMATION: A or T
<220> FEATURE:
<221> NAME/KEY: SITE
<222> LOCATION: 32
<223> OTHER INFORMATION: P or Y

<400> SEQUENCE: 5

Cys Ser Asn Leu Ser Thr Cys Val Leu Gly Xaa Leu Ser Gln Glu Leu
1               5                   10                  15

His Xaa Leu Gln Thr Xaa Pro Arg Thr Asp Val Gly Ala Asn Xaa Xaa
            20                  25                  30

<210> SEQ ID NO 6
<211> LENGTH: 32
<212> TYPE: PRT
<213> ORGANISM: Artificial Sequence
<220> FEATURE:
<223> OTHER INFORMATION: Synthetic Construct
<220> FEATURE:
<221> NAME/KEY: SITE
<222> LOCATION: 15
<223> OTHER INFORMATION: D or E
<220> FEATURE:
<221> NAME/KEY: SITE
<222> LOCATION: 22
<223> OTHER INFORMATION: F or Y

<400> SEQUENCE: 6

Cys Ala Ser Leu Ser Thr Cys Val Leu Gly Arg Leu Ser Gln Xaa Leu
1               5                   10                  15

His Arg Leu Gln Thr Xaa Pro Arg Thr Asp Val Gly Ala Asn Ala Pro
            20                  25                  30

<210> SEQ ID NO 7
<211> LENGTH: 32
<212> TYPE: PRT
<213> ORGANISM: Artificial Sequence
<220> FEATURE:
<223> OTHER INFORMATION: Synthetic Construct
<220> FEATURE:
<221> NAME/KEY: SITE
<222> LOCATION: 15
<223> OTHER INFORMATION: D or E
<220> FEATURE:
<221> NAME/KEY: SITE
<222> LOCATION: 22
<223> OTHER INFORMATION: F or Y

<400> SEQUENCE: 7

Cys Ala Ser Leu Ser Thr Cys Met Leu Gly Lys Leu Thr Gln Xaa Leu
1               5                   10                  15

His Lys Leu Gln Thr Xaa Pro Arg Thr Asp Val Gly Ala Asn Ala Pro
            20                  25                  30

<210> SEQ ID NO 8
<211> LENGTH: 32
<212> TYPE: PRT
<213> ORGANISM: Artificial Sequence
<220> FEATURE:
<223> OTHER INFORMATION: Synthetic Construct (KBP-056/057)
```

<220> FEATURE:
<221> NAME/KEY: SITE
<222> LOCATION: 15
<223> OTHER INFORMATION: D or E
<220> FEATURE:
<221> NAME/KEY: SITE
<222> LOCATION: 22
<223> OTHER INFORMATION: F or Y

<400> SEQUENCE: 8

Cys Ala Ser Leu Ser Thr Cys Val Leu Gly Lys Leu Ser Gln Xaa Leu
1               5                   10                  15

His Lys Leu Gln Thr Xaa Pro Lys Thr Asp Val Gly Ala Asn Ala Pro
            20                  25                  30

<210> SEQ ID NO 9
<211> LENGTH: 32
<212> TYPE: PRT
<213> ORGANISM: Artificial Sequence
<220> FEATURE:
<223> OTHER INFORMATION: Synthetic Construct (KBP-088/089)
<220> FEATURE:
<221> NAME/KEY: SITE
<222> LOCATION: 15
<223> OTHER INFORMATION: D or E
<220> FEATURE:
<221> NAME/KEY: SITE
<222> LOCATION: 22
<223> OTHER INFORMATION: F or Y

<400> SEQUENCE: 9

Cys Ser Asn Leu Ser Thr Cys Met Leu Gly Arg Leu Ser Gln Xaa Leu
1               5                   10                  15

His Arg Leu Gln Thr Xaa Pro Lys Thr Asp Val Gly Ala Asn Ala Pro
            20                  25                  30

<210> SEQ ID NO 10
<211> LENGTH: 32
<212> TYPE: PRT
<213> ORGANISM: Artificial Sequence
<220> FEATURE:
<223> OTHER INFORMATION: Synthetic Construct
<220> FEATURE:
<221> NAME/KEY: SITE
<222> LOCATION: 15
<223> OTHER INFORMATION: D or E
<220> FEATURE:
<221> NAME/KEY: SITE
<222> LOCATION: 22
<223> OTHER INFORMATION: F or Y

<400> SEQUENCE: 10

Cys Ala Ser Leu Ser Thr Cys Met Leu Gly Arg Leu Ser Gln Xaa Leu
1               5                   10                  15

His Arg Leu Gln Thr Xaa Pro Lys Thr Asp Val Gly Ala Asn Ala Pro
            20                  25                  30

<210> SEQ ID NO 11
<211> LENGTH: 32
<212> TYPE: PRT
<213> ORGANISM: Artificial Sequence
<220> FEATURE:
<223> OTHER INFORMATION: Synthetic Construct
<220> FEATURE:
<221> NAME/KEY: SITE
<222> LOCATION: 15
<223> OTHER INFORMATION: D or E

```
<220> FEATURE:
<221> NAME/KEY: SITE
<222> LOCATION: 22
<223> OTHER INFORMATION: F or Y

<400> SEQUENCE: 11

Cys Ala Ser Leu Ser Thr Cys Met Leu Gly Lys Leu Thr Gln Xaa Leu
1               5                   10                  15

His Lys Leu Gln Thr Xaa Pro Lys Thr Asp Val Gly Ala Asn Ala Pro
            20                  25                  30

<210> SEQ ID NO 12
<211> LENGTH: 32
<212> TYPE: PRT
<213> ORGANISM: Artificial Sequence
<220> FEATURE:
<223> OTHER INFORMATION: Synthetic Construct
<220> FEATURE:
<221> NAME/KEY: SITE
<222> LOCATION: 15
<223> OTHER INFORMATION: D or E
<220> FEATURE:
<221> NAME/KEY: SITE
<222> LOCATION: 22
<223> OTHER INFORMATION: F or Y

<400> SEQUENCE: 12

Cys Ala Ser Leu Ser Thr Cys Val Leu Gly Lys Leu Ser Gln Xaa Leu
1               5                   10                  15

His Lys Leu Gln Thr Xaa Pro Arg Thr Asp Val Gly Ala Asn Ala Pro
            20                  25                  30

<210> SEQ ID NO 13
<211> LENGTH: 32
<212> TYPE: PRT
<213> ORGANISM: Artificial Sequence
<220> FEATURE:
<223> OTHER INFORMATION: Synthetic Construct
<220> FEATURE:
<221> NAME/KEY: SITE
<222> LOCATION: 15
<223> OTHER INFORMATION: D or E
<220> FEATURE:
<221> NAME/KEY: SITE
<222> LOCATION: 22
<223> OTHER INFORMATION: F or Y

<400> SEQUENCE: 13

Cys Ser Asn Leu Ser Thr Cys Val Leu Gly Arg Leu Ser Gln Xaa Leu
1               5                   10                  15

His Arg Leu Gln Thr Xaa Pro Lys Thr Asp Val Gly Ala Asn Ala Pro
            20                  25                  30

<210> SEQ ID NO 14
<211> LENGTH: 32
<212> TYPE: PRT
<213> ORGANISM: Artificial Sequence
<220> FEATURE:
<223> OTHER INFORMATION: Synthetic Construct (KBP-017)
<220> FEATURE:
<221> NAME/KEY: SITE
<222> LOCATION: 15
<223> OTHER INFORMATION: D or E
<220> FEATURE:
<221> NAME/KEY: SITE
<222> LOCATION: 22
<223> OTHER INFORMATION: F or Y
```

```
<400> SEQUENCE: 14

Cys Ala Ser Leu Ser Thr Cys Val Leu Gly Lys Leu Ser Gln Xaa Leu
1               5                   10                  15

His Lys Leu Gln Ser Xaa Pro Lys Thr Asp Val Gly Ala Asn Ala Pro
            20                  25                  30

<210> SEQ ID NO 15
<211> LENGTH: 32
<212> TYPE: PRT
<213> ORGANISM: Artificial Sequence
<220> FEATURE:
<223> OTHER INFORMATION: Synthetic Construct (KBP-018)
<220> FEATURE:
<221> NAME/KEY: SITE
<222> LOCATION: 15
<223> OTHER INFORMATION: D or E
<220> FEATURE:
<221> NAME/KEY: SITE
<222> LOCATION: 22
<223> OTHER INFORMATION: F or Y

<400> SEQUENCE: 15

Cys Ala Ser Leu Ser Thr Cys Val Leu Gly Lys Leu Ser Gln Xaa Leu
1               5                   10                  15

His Lys Leu Gln Thr Xaa Pro Lys Thr Asp Val Gly Ala Asn Ala Pro
            20                  25                  30

<210> SEQ ID NO 16
<211> LENGTH: 32
<212> TYPE: PRT
<213> ORGANISM: Artificial Sequence
<220> FEATURE:
<223> OTHER INFORMATION: Synthetic Construct (KBP-011)

<400> SEQUENCE: 16

Cys Ala Ser Leu Ser Thr Cys Val Leu Gly Arg Leu Ser Gln Glu Leu
1               5                   10                  15

His Arg Leu Gln Thr Phe Pro Arg Thr Asp Val Gly Ala Asn Ala Pro
            20                  25                  30

<210> SEQ ID NO 17
<211> LENGTH: 32
<212> TYPE: PRT
<213> ORGANISM: Artificial Sequence
<220> FEATURE:
<223> OTHER INFORMATION: Synthetic Construct

<400> SEQUENCE: 17

Cys Ala Ser Leu Ser Thr Cys Met Leu Gly Lys Leu Thr Gln Glu Leu
1               5                   10                  15

His Lys Leu Gln Thr Phe Pro Arg Thr Asp Val Gly Ala Asn Ala Pro
            20                  25                  30

<210> SEQ ID NO 18
<211> LENGTH: 32
<212> TYPE: PRT
<213> ORGANISM: Artificial Sequence
<220> FEATURE:
<223> OTHER INFORMATION: Synthetic Construct (KBP-018)

<400> SEQUENCE: 18

Cys Ala Ser Leu Ser Thr Cys Val Leu Gly Lys Leu Ser Gln Glu Leu
1               5                   10                  15

His Lys Leu Gln Thr Phe Pro Lys Thr Asp Val Gly Ala Asn Ala Pro
            20                  25                  30
```

```
<210> SEQ ID NO 19
<211> LENGTH: 32
<212> TYPE: PRT
<213> ORGANISM: Artificial Sequence
<220> FEATURE:
<223> OTHER INFORMATION: Synthetic Construct (KBP-088)

<400> SEQUENCE: 19

Cys Ser Asn Leu Ser Thr Cys Met Leu Gly Arg Leu Ser Gln Glu Leu
1               5                   10                  15

His Arg Leu Gln Thr Phe Pro Lys Thr Asp Val Gly Ala Asn Ala Pro
            20                  25                  30

<210> SEQ ID NO 20
<211> LENGTH: 32
<212> TYPE: PRT
<213> ORGANISM: Artificial Sequence
<220> FEATURE:
<223> OTHER INFORMATION: Synthetic Construct

<400> SEQUENCE: 20

Cys Ala Ser Leu Ser Thr Cys Val Leu Gly Arg Leu Ser Gln Glu Leu
1               5                   10                  15

His Arg Leu Gln Thr Tyr Pro Arg Thr Asp Val Gly Ala Asn Ala Pro
            20                  25                  30

<210> SEQ ID NO 21
<211> LENGTH: 32
<212> TYPE: PRT
<213> ORGANISM: Artificial Sequence
<220> FEATURE:
<223> OTHER INFORMATION: Synthetic Construct

<400> SEQUENCE: 21

Cys Ala Ser Leu Ser Thr Cys Met Leu Gly Lys Leu Thr Gln Glu Leu
1               5                   10                  15

His Lys Leu Gln Thr Tyr Pro Arg Thr Asp Val Gly Ala Asn Ala Pro
            20                  25                  30

<210> SEQ ID NO 22
<211> LENGTH: 32
<212> TYPE: PRT
<213> ORGANISM: Artificial Sequence
<220> FEATURE:
<223> OTHER INFORMATION: Synthetic Construct

<400> SEQUENCE: 22

Cys Ala Ser Leu Ser Thr Cys Val Leu Gly Lys Leu Ser Gln Glu Leu
1               5                   10                  15

His Lys Leu Gln Thr Tyr Pro Lys Thr Asp Val Gly Ala Asn Ala Pro
            20                  25                  30

<210> SEQ ID NO 23
<211> LENGTH: 32
<212> TYPE: PRT
<213> ORGANISM: Artificial Sequence
<220> FEATURE:
<223> OTHER INFORMATION: Synthetic Construct (KBP-021)

<400> SEQUENCE: 23

Cys Ser Asn Leu Ser Thr Cys Met Leu Gly Arg Leu Ser Gln Glu Leu
1               5                   10                  15

His Arg Leu Gln Thr Tyr Pro Lys Thr Asp Val Gly Ala Asn Ala Pro
            20                  25                  30
```

```
<210> SEQ ID NO 24
<211> LENGTH: 32
<212> TYPE: PRT
<213> ORGANISM: Artificial Sequence
<220> FEATURE:
<223> OTHER INFORMATION: Synthetic Construct

<400> SEQUENCE: 24

Cys Ala Ser Leu Ser Thr Cys Val Leu Gly Arg Leu Ser Gln Asp Leu
1               5                   10                  15

His Arg Leu Gln Thr Phe Pro Arg Thr Asp Val Gly Ala Asn Ala Pro
            20                  25                  30

<210> SEQ ID NO 25
<211> LENGTH: 32
<212> TYPE: PRT
<213> ORGANISM: Artificial Sequence
<220> FEATURE:
<223> OTHER INFORMATION: Synthetic Construct

<400> SEQUENCE: 25

Cys Ala Ser Leu Ser Thr Cys Met Leu Gly Lys Leu Thr Gln Asp Leu
1               5                   10                  15

His Lys Leu Gln Thr Phe Pro Arg Thr Asp Val Gly Ala Asn Ala Pro
            20                  25                  30

<210> SEQ ID NO 26
<211> LENGTH: 32
<212> TYPE: PRT
<213> ORGANISM: Artificial Sequence
<220> FEATURE:
<223> OTHER INFORMATION: Synthetic Construct (KBP-056)

<400> SEQUENCE: 26

Cys Ala Ser Leu Ser Thr Cys Val Leu Gly Lys Leu Ser Gln Asp Leu
1               5                   10                  15

His Lys Leu Gln Thr Phe Pro Lys Thr Asp Val Gly Ala Asn Ala Pro
            20                  25                  30

<210> SEQ ID NO 27
<211> LENGTH: 32
<212> TYPE: PRT
<213> ORGANISM: Artificial Sequence
<220> FEATURE:
<223> OTHER INFORMATION: Synthetic Construct

<400> SEQUENCE: 27

Cys Ser Asn Leu Ser Thr Cys Met Leu Gly Arg Leu Ser Gln Asp Leu
1               5                   10                  15

His Arg Leu Gln Thr Phe Pro Lys Thr Asp Val Gly Ala Asn Ala Pro
            20                  25                  30

<210> SEQ ID NO 28
<211> LENGTH: 32
<212> TYPE: PRT
<213> ORGANISM: Artificial Sequence
<220> FEATURE:
<223> OTHER INFORMATION: Synthetic Construct

<400> SEQUENCE: 28

Cys Ala Ser Leu Ser Thr Cys Val Leu Gly Arg Leu Ser Gln Asp Leu
1               5                   10                  15

His Arg Leu Gln Thr Tyr Pro Arg Thr Asp Val Gly Ala Asn Ala Pro
            20                  25                  30
```

```
<210> SEQ ID NO 29
<211> LENGTH: 32
<212> TYPE: PRT
<213> ORGANISM: Artificial Sequence
<220> FEATURE:
<223> OTHER INFORMATION: Synthetic Construct

<400> SEQUENCE: 29

Cys Ala Ser Leu Ser Thr Cys Met Leu Gly Lys Leu Thr Gln Asp Leu
1               5                   10                  15

His Lys Leu Gln Thr Tyr Pro Arg Thr Asp Val Gly Ala Asn Ala Pro
            20                  25                  30

<210> SEQ ID NO 30
<211> LENGTH: 32
<212> TYPE: PRT
<213> ORGANISM: Artificial Sequence
<220> FEATURE:
<223> OTHER INFORMATION: Synthetic Construct (KBP-057)

<400> SEQUENCE: 30

Cys Ala Ser Leu Ser Thr Cys Val Leu Gly Lys Leu Ser Gln Asp Leu
1               5                   10                  15

His Lys Leu Gln Thr Tyr Pro Lys Thr Asp Val Gly Ala Asn Ala Pro
            20                  25                  30

<210> SEQ ID NO 31
<211> LENGTH: 32
<212> TYPE: PRT
<213> ORGANISM: Artificial Sequence
<220> FEATURE:
<223> OTHER INFORMATION: Synthetic Construct (KBP-089)

<400> SEQUENCE: 31

Cys Ser Asn Leu Ser Thr Cys Met Leu Gly Arg Leu Ser Gln Asp Leu
1               5                   10                  15

His Arg Leu Gln Thr Tyr Pro Lys Thr Asp Val Gly Ala Asn Ala Pro
            20                  25                  30

<210> SEQ ID NO 32
<211> LENGTH: 32
<212> TYPE: PRT
<213> ORGANISM: Artificial Sequence
<220> FEATURE:
<223> OTHER INFORMATION: Synthetic Construct

<400> SEQUENCE: 32

Cys Ala Ser Leu Ser Thr Cys Val Leu Gly Arg Leu Ser Gln Glu Leu
1               5                   10                  15

His Arg Leu Gln Ser Phe Pro Arg Thr Asp Val Gly Ala Asn Ala Pro
            20                  25                  30

<210> SEQ ID NO 33
<211> LENGTH: 32
<212> TYPE: PRT
<213> ORGANISM: Artificial Sequence
<220> FEATURE:
<223> OTHER INFORMATION: Synthetic Construct

<400> SEQUENCE: 33

Cys Ala Ser Leu Ser Thr Cys Met Leu Gly Lys Leu Thr Gln Glu Leu
1               5                   10                  15

His Lys Leu Gln Ser Phe Pro Arg Thr Asp Val Gly Ala Asn Ala Pro
            20                  25                  30
```

<210> SEQ ID NO 34
<211> LENGTH: 32
<212> TYPE: PRT
<213> ORGANISM: Artificial Sequence
<220> FEATURE:
<223> OTHER INFORMATION: Synthetic Construct

<400> SEQUENCE: 34

Cys Ala Ser Leu Ser Thr Cys Val Leu Gly Lys Leu Ser Gln Glu Leu
1               5                   10                  15

His Lys Leu Gln Ser Phe Pro Lys Thr Asp Val Gly Ala Asn Ala Pro
            20                  25                  30

<210> SEQ ID NO 35
<211> LENGTH: 32
<212> TYPE: PRT
<213> ORGANISM: Artificial Sequence
<220> FEATURE:
<223> OTHER INFORMATION: Synthetic Construct

<400> SEQUENCE: 35

Cys Ser Asn Leu Ser Thr Cys Met Leu Gly Arg Leu Ser Gln Glu Leu
1               5                   10                  15

His Arg Leu Gln Ser Phe Pro Lys Thr Asp Val Gly Ala Asn Ala Pro
            20                  25                  30

<210> SEQ ID NO 36
<211> LENGTH: 32
<212> TYPE: PRT
<213> ORGANISM: Artificial Sequence
<220> FEATURE:
<223> OTHER INFORMATION: Synthetic Construct

<400> SEQUENCE: 36

Cys Ala Ser Leu Ser Thr Cys Val Leu Gly Arg Leu Ser Gln Glu Leu
1               5                   10                  15

His Arg Leu Gln Ser Tyr Pro Arg Thr Asp Val Gly Ala Asn Ala Pro
            20                  25                  30

<210> SEQ ID NO 37
<211> LENGTH: 32
<212> TYPE: PRT
<213> ORGANISM: Artificial Sequence
<220> FEATURE:
<223> OTHER INFORMATION: Synthetic Construct

<400> SEQUENCE: 37

Cys Ala Ser Leu Ser Thr Cys Met Leu Gly Lys Leu Thr Gln Glu Leu
1               5                   10                  15

His Lys Leu Gln Ser Tyr Pro Arg Thr Asp Val Gly Ala Asn Ala Pro
            20                  25                  30

<210> SEQ ID NO 38
<211> LENGTH: 32
<212> TYPE: PRT
<213> ORGANISM: Artificial Sequence
<220> FEATURE:
<223> OTHER INFORMATION: Synthetic Sequence

<400> SEQUENCE: 38

Cys Ala Ser Leu Ser Thr Cys Val Leu Gly Lys Leu Ser Gln Glu Leu
1               5                   10                  15

His Lys Leu Gln Ser Tyr Pro Lys Thr Asp Val Gly Ala Asn Ala Pro
            20                  25                  30

```
<210> SEQ ID NO 39
<211> LENGTH: 32
<212> TYPE: PRT
<213> ORGANISM: Artificial Sequence
<220> FEATURE:
<223> OTHER INFORMATION: Synthetic Construct

<400> SEQUENCE: 39

Cys Ser Asn Leu Ser Thr Cys Met Leu Gly Arg Leu Ser Gln Glu Leu
1               5                   10                  15

His Arg Leu Gln Ser Tyr Pro Lys Thr Asp Val Gly Ala Asn Ala Pro
            20                  25                  30

<210> SEQ ID NO 40
<211> LENGTH: 32
<212> TYPE: PRT
<213> ORGANISM: Artificial Sequence
<220> FEATURE:
<223> OTHER INFORMATION: Synthetic Construct

<400> SEQUENCE: 40

Cys Ala Ser Leu Ser Thr Cys Val Leu Gly Arg Leu Ser Gln Asp Leu
1               5                   10                  15

His Arg Leu Gln Ser Phe Pro Arg Thr Asp Val Gly Ala Asn Ala Pro
            20                  25                  30

<210> SEQ ID NO 41
<211> LENGTH: 32
<212> TYPE: PRT
<213> ORGANISM: Artificial Sequence
<220> FEATURE:
<223> OTHER INFORMATION: Synthetic Construct

<400> SEQUENCE: 41

Cys Ala Ser Leu Ser Thr Cys Met Leu Gly Lys Leu Thr Gln Asp Leu
1               5                   10                  15

His Lys Leu Gln Ser Phe Pro Arg Thr Asp Val Gly Ala Asn Ala Pro
            20                  25                  30

<210> SEQ ID NO 42
<211> LENGTH: 32
<212> TYPE: PRT
<213> ORGANISM: Artificial Sequence
<220> FEATURE:
<223> OTHER INFORMATION: Synthetic Construct

<400> SEQUENCE: 42

Cys Ala Ser Leu Ser Thr Cys Val Leu Gly Lys Leu Ser Gln Asp Leu
1               5                   10                  15

His Lys Leu Gln Ser Phe Pro Lys Thr Asp Val Gly Ala Asn Ala Pro
            20                  25                  30

<210> SEQ ID NO 43
<211> LENGTH: 32
<212> TYPE: PRT
<213> ORGANISM: Artificial Sequence
<220> FEATURE:
<223> OTHER INFORMATION: Synthetic Construct

<400> SEQUENCE: 43

Cys Ser Asn Leu Ser Thr Cys Met Leu Gly Arg Leu Ser Gln Asp Leu
1               5                   10                  15

His Arg Leu Gln Ser Phe Pro Lys Thr Asp Val Gly Ala Asn Ala Pro
            20                  25                  30
```

<210> SEQ ID NO 44
<211> LENGTH: 32
<212> TYPE: PRT
<213> ORGANISM: Artificial Sequence
<220> FEATURE:
<223> OTHER INFORMATION: Synthetic Construct

<400> SEQUENCE: 44

Cys Ala Ser Leu Ser Thr Cys Val Leu Gly Arg Leu Ser Gln Asp Leu
1               5                   10                  15

His Arg Leu Gln Ser Tyr Pro Arg Thr Asp Val Gly Ala Asn Ala Pro
            20                  25                  30

<210> SEQ ID NO 45
<211> LENGTH: 32
<212> TYPE: PRT
<213> ORGANISM: Artificial Sequence
<220> FEATURE:
<223> OTHER INFORMATION: Synthetic Construct

<400> SEQUENCE: 45

Cys Ala Ser Leu Ser Thr Cys Met Leu Gly Lys Leu Thr Gln Asp Leu
1               5                   10                  15

His Lys Leu Gln Ser Tyr Pro Arg Thr Asp Val Gly Ala Asn Ala Pro
            20                  25                  30

<210> SEQ ID NO 46
<211> LENGTH: 32
<212> TYPE: PRT
<213> ORGANISM: Artificial Sequence
<220> FEATURE:
<223> OTHER INFORMATION: Synthetic Construct (KBP-017)

<400> SEQUENCE: 46

Cys Ala Ser Leu Ser Thr Cys Val Leu Gly Lys Leu Ser Gln Asp Leu
1               5                   10                  15

His Lys Leu Gln Ser Tyr Pro Lys Thr Asp Val Gly Ala Asn Ala Pro
            20                  25                  30

<210> SEQ ID NO 47
<211> LENGTH: 32
<212> TYPE: PRT
<213> ORGANISM: Artificial Sequence
<220> FEATURE:
<223> OTHER INFORMATION: Synthetic Construct

<400> SEQUENCE: 47

Cys Ser Asn Leu Ser Thr Cys Met Leu Gly Arg Leu Ser Gln Asp Leu
1               5                   10                  15

His Arg Leu Gln Ser Tyr Pro Lys Thr Asp Val Gly Ala Asn Ala Pro
            20                  25                  30

<210> SEQ ID NO 48
<211> LENGTH: 32
<212> TYPE: PRT
<213> ORGANISM: Artificial Sequence
<220> FEATURE:
<223> OTHER INFORMATION: Synthetic Construct

<400> SEQUENCE: 48

Cys Ser Asn Leu Ser Thr Cys Val Leu Gly Lys Leu Ser Gln Glu Leu
1               5                   10                  15

His Lys Leu Gln Thr Tyr Pro Arg Thr Asp Val Gly Ala Asn Ala Pro
            20                  25                  30

-continued

```
<210> SEQ ID NO 49
<211> LENGTH: 32
<212> TYPE: PRT
<213> ORGANISM: Artificial Sequence
<220> FEATURE:
<223> OTHER INFORMATION: Synthetic Construct

<400> SEQUENCE: 49

Cys Ala Ser Leu Ser Thr Cys Met Leu Gly Arg Leu Ser Gln Asp Leu
1               5                   10                  15

His Arg Leu Gln Thr Tyr Pro Lys Thr Asp Val Gly Ala Asn Ala Pro
            20                  25                  30

<210> SEQ ID NO 50
<211> LENGTH: 32
<212> TYPE: PRT
<213> ORGANISM: Artificial Sequence
<220> FEATURE:
<223> OTHER INFORMATION: Synthetic Construct (KBP-011)
<220> FEATURE:
<221> NAME/KEY: MOD_RES
<222> LOCATION: 1
<223> OTHER INFORMATION: ACETYLATION
<220> FEATURE:
<221> NAME/KEY: MOD_RES
<222> LOCATION: 32
<223> OTHER INFORMATION: AMIDATION

<400> SEQUENCE: 50

Cys Ala Ser Leu Ser Thr Cys Val Leu Gly Arg Leu Ser Gln Glu Leu
1               5                   10                  15

His Arg Leu Gln Thr Phe Pro Arg Thr Asp Val Gly Ala Asn Ala Pro
            20                  25                  30

<210> SEQ ID NO 51
<211> LENGTH: 32
<212> TYPE: PRT
<213> ORGANISM: Artificial Sequence
<220> FEATURE:
<223> OTHER INFORMATION: Synthetic Construct (KBP-017)
<220> FEATURE:
<221> NAME/KEY: MOD_RES
<222> LOCATION: 1
<223> OTHER INFORMATION: ACETYLATION
<220> FEATURE:
<221> NAME/KEY: MOD_RES
<222> LOCATION: 32
<223> OTHER INFORMATION: AMIDATION

<400> SEQUENCE: 51

Cys Ala Ser Leu Ser Thr Cys Val Leu Gly Lys Leu Ser Gln Asp Leu
1               5                   10                  15

His Lys Leu Gln Ser Tyr Pro Lys Thr Asp Val Gly Ala Asn Ala Pro
            20                  25                  30

<210> SEQ ID NO 52
<211> LENGTH: 32
<212> TYPE: PRT
<213> ORGANISM: Artificial Sequence
<220> FEATURE:
<223> OTHER INFORMATION: Synthetic Construct (KBP-018)
<220> FEATURE:
<221> NAME/KEY: MOD_RES
<222> LOCATION: 1
<223> OTHER INFORMATION: ACETYLATION
<220> FEATURE:
<221> NAME/KEY: MOD_RES
<222> LOCATION: 32
<223> OTHER INFORMATION: AMIDATION
```

```
<400> SEQUENCE: 52

Cys Ala Ser Leu Ser Thr Cys Val Leu Gly Lys Leu Ser Gln Glu Leu
1               5                   10                  15

His Lys Leu Gln Thr Phe Pro Lys Thr Asp Val Gly Ala Asn Ala Pro
            20                  25                  30

<210> SEQ ID NO 53
<211> LENGTH: 32
<212> TYPE: PRT
<213> ORGANISM: Artificial Sequence
<220> FEATURE:
<223> OTHER INFORMATION: Synthetic Construct (KBP-023)
<220> FEATURE:
<221> NAME/KEY: MOD_RES
<222> LOCATION: 1
<223> OTHER INFORMATION: ACETYLATION
<220> FEATURE:
<221> NAME/KEY: MOD_RES
<222> LOCATION: 32
<223> OTHER INFORMATION: AMIDATION

<400> SEQUENCE: 53

Cys Ala Ser Leu Ser Thr Cys Met Leu Gly Lys Leu Thr Gln Glu Leu
1               5                   10                  15

His Lys Leu Gln Thr Phe Pro Arg Thr Asp Val Gly Ala Asn Ala Pro
            20                  25                  30

<210> SEQ ID NO 54
<211> LENGTH: 32
<212> TYPE: PRT
<213> ORGANISM: Artificial Sequence
<220> FEATURE:
<223> OTHER INFORMATION: Synthetic Construct (KBP-042)
<220> FEATURE:
<221> NAME/KEY: MOD_RES
<222> LOCATION: 1
<223> OTHER INFORMATION: ACETYLATION
<220> FEATURE:
<221> NAME/KEY: MOD_RES
<222> LOCATION: 32
<223> OTHER INFORMATION: AMIDATION

<400> SEQUENCE: 54

Cys Ser Asn Leu Ser Thr Cys Val Leu Gly Lys Leu Ser Gln Glu Leu
1               5                   10                  15

His Lys Leu Gln Thr Tyr Pro Arg Thr Asp Val Gly Ala Asn Ala Pro
            20                  25                  30

<210> SEQ ID NO 55
<211> LENGTH: 32
<212> TYPE: PRT
<213> ORGANISM: Artificial Sequence
<220> FEATURE:
<223> OTHER INFORMATION: Synthetic Construct (KBP-056)
<220> FEATURE:
<221> NAME/KEY: MOD_RES
<222> LOCATION: 1
<223> OTHER INFORMATION: ACETYLATION
<220> FEATURE:
<221> NAME/KEY: MOD_RES
<222> LOCATION: 32
<223> OTHER INFORMATION: AMIDATION

<400> SEQUENCE: 55

Cys Ala Ser Leu Ser Thr Cys Val Leu Gly Lys Leu Ser Gln Asp Leu
1               5                   10                  15

His Lys Leu Gln Thr Phe Pro Lys Thr Asp Val Gly Ala Asn Ala Pro
            20                  25                  30
```

```
<210> SEQ ID NO 56
<211> LENGTH: 32
<212> TYPE: PRT
<213> ORGANISM: Artificial Sequence
<220> FEATURE:
<223> OTHER INFORMATION: Synthetic Construct (KBP-057)
<220> FEATURE:
<221> NAME/KEY: MOD_RES
<222> LOCATION: 1
<223> OTHER INFORMATION: ACETYLATION
<220> FEATURE:
<221> NAME/KEY: MOD_RES
<222> LOCATION: 32
<223> OTHER INFORMATION: AMIDATION

<400> SEQUENCE: 56

Cys Ala Ser Leu Ser Thr Cys Val Leu Gly Lys Leu Ser Gln Asp Leu
1               5                   10                  15

His Lys Leu Gln Thr Tyr Pro Lys Thr Asp Val Gly Ala Asn Ala Pro
            20                  25                  30

<210> SEQ ID NO 57
<211> LENGTH: 32
<212> TYPE: PRT
<213> ORGANISM: Artificial Sequence
<220> FEATURE:
<223> OTHER INFORMATION: Synthetic Construct (KBP-088)
<220> FEATURE:
<221> NAME/KEY: MOD_RES
<222> LOCATION: 1
<223> OTHER INFORMATION: ACETYLATION
<220> FEATURE:
<221> NAME/KEY: MOD_RES
<222> LOCATION: 32
<223> OTHER INFORMATION: AMIDATION

<400> SEQUENCE: 57

Cys Ser Asn Leu Ser Thr Cys Met Leu Gly Arg Leu Ser Gln Glu Leu
1               5                   10                  15

His Arg Leu Gln Thr Phe Pro Lys Thr Asp Val Gly Ala Asn Ala Pro
            20                  25                  30

<210> SEQ ID NO 58
<211> LENGTH: 32
<212> TYPE: PRT
<213> ORGANISM: Artificial Sequence
<220> FEATURE:
<223> OTHER INFORMATION: Synthetic Construct (KBP-089)
<220> FEATURE:
<221> NAME/KEY: MOD_RES
<222> LOCATION: 1
<223> OTHER INFORMATION: ACETYLATION
<220> FEATURE:
<221> NAME/KEY: MOD_RES
<222> LOCATION: 32
<223> OTHER INFORMATION: AMIDATION

<400> SEQUENCE: 58

Cys Ser Asn Leu Ser Thr Cys Met Leu Gly Arg Leu Ser Gln Asp Leu
1               5                   10                  15

His Arg Leu Gln Thr Tyr Pro Lys Thr Asp Val Gly Ala Asn Ala Pro
            20                  25                  30

<210> SEQ ID NO 59
<211> LENGTH: 32
<212> TYPE: PRT
<213> ORGANISM: Artificial Sequence
<220> FEATURE:
<223> OTHER INFORMATION: Synthetic Construct
```

```
<220> FEATURE:
<221> NAME/KEY: SITE
<222> LOCATION: 15
<223> OTHER INFORMATION: D or E
<220> FEATURE:
<221> NAME/KEY: SITE
<222> LOCATION: 22
<223> OTHER INFORMATION: F or Y

<400> SEQUENCE: 59

Cys Ala Ser Leu Ser Thr Cys Val Leu Gly Arg Leu Ser Gln Xaa Leu
1               5                   10                  15

His Arg Leu Gln Thr Xaa Pro Lys Thr Asp Val Gly Ala Asn Ala Tyr
            20                  25                  30

<210> SEQ ID NO 60
<211> LENGTH: 32
<212> TYPE: PRT
<213> ORGANISM: Artificial Sequence
<220> FEATURE:
<223> OTHER INFORMATION: Synthetic Construct
<220> FEATURE:
<221> NAME/KEY: SITE
<222> LOCATION: 15
<223> OTHER INFORMATION: D or E
<220> FEATURE:
<221> NAME/KEY: SITE
<222> LOCATION: 22
<223> OTHER INFORMATION: F or Y

<400> SEQUENCE: 60

Cys Ala Ser Leu Ser Thr Cys Met Leu Gly Lys Leu Thr Gln Xaa Leu
1               5                   10                  15

His Lys Leu Gln Thr Xaa Pro Lys Thr Asp Val Gly Ala Asn Ala Tyr
            20                  25                  30

<210> SEQ ID NO 61
<211> LENGTH: 32
<212> TYPE: PRT
<213> ORGANISM: Artificial Sequence
<220> FEATURE:
<223> OTHER INFORMATION: Synthetic Construct
<220> FEATURE:
<221> NAME/KEY: SITE
<222> LOCATION: 15
<223> OTHER INFORMATION: D or E
<220> FEATURE:
<221> NAME/KEY: SITE
<222> LOCATION: 22
<223> OTHER INFORMATION: F or Y

<400> SEQUENCE: 61

Cys Ala Ser Leu Ser Thr Cys Val Leu Gly Lys Leu Ser Gln Xaa Leu
1               5                   10                  15

His Lys Leu Gln Thr Xaa Pro Lys Thr Asp Val Gly Ala Asn Ala Tyr
            20                  25                  30

<210> SEQ ID NO 62
<211> LENGTH: 32
<212> TYPE: PRT
<213> ORGANISM: Artificial Sequence
<220> FEATURE:
<223> OTHER INFORMATION: Synthetic Construct
<220> FEATURE:
<221> NAME/KEY: SITE
<222> LOCATION: 15
<223> OTHER INFORMATION: D or E
```

```
<220> FEATURE:
<221> NAME/KEY: SITE
<222> LOCATION: 22
<223> OTHER INFORMATION: F or Y

<400> SEQUENCE: 62

Cys Ser Asn Leu Ser Thr Cys Met Leu Gly Arg Leu Ser Gln Xaa Leu
1               5                   10                  15

His Arg Leu Gln Thr Xaa Pro Lys Thr Asp Val Gly Ala Asn Ala Tyr
            20                  25                  30

<210> SEQ ID NO 63
<211> LENGTH: 32
<212> TYPE: PRT
<213> ORGANISM: Artificial Sequence
<220> FEATURE:
<223> OTHER INFORMATION: Synthetic Construct
<220> FEATURE:
<221> NAME/KEY: SITE
<222> LOCATION: 15
<223> OTHER INFORMATION: D or E
<220> FEATURE:
<221> NAME/KEY: SITE
<222> LOCATION: 22
<223> OTHER INFORMATION: F or Y

<400> SEQUENCE: 63

Cys Ala Ser Leu Ser Thr Cys Val Leu Gly Arg Leu Ser Gln Xaa Leu
1               5                   10                  15

His Arg Leu Gln Thr Xaa Pro Arg Thr Asp Val Gly Ala Asn Ala Tyr
            20                  25                  30

<210> SEQ ID NO 64
<211> LENGTH: 32
<212> TYPE: PRT
<213> ORGANISM: Artificial Sequence
<220> FEATURE:
<223> OTHER INFORMATION: Synthetic Construct
<220> FEATURE:
<221> NAME/KEY: SITE
<222> LOCATION: 15
<223> OTHER INFORMATION: D or E
<220> FEATURE:
<221> NAME/KEY: SITE
<222> LOCATION: 22
<223> OTHER INFORMATION: F or Y

<400> SEQUENCE: 64

Cys Ala Ser Leu Ser Thr Cys Met Leu Gly Lys Leu Thr Gln Xaa Leu
1               5                   10                  15

His Lys Leu Gln Thr Xaa Pro Arg Thr Asp Val Gly Ala Asn Ala Tyr
            20                  25                  30

<210> SEQ ID NO 65
<211> LENGTH: 32
<212> TYPE: PRT
<213> ORGANISM: Artificial Sequence
<220> FEATURE:
<223> OTHER INFORMATION: Synthetic Construct
<220> FEATURE:
<221> NAME/KEY: SITE
<222> LOCATION: 15
<223> OTHER INFORMATION: D or E
<220> FEATURE:
<221> NAME/KEY: SITE
<222> LOCATION: 22
<223> OTHER INFORMATION: F or Y
```

```
<400> SEQUENCE: 65

Cys Ala Ser Leu Ser Thr Cys Val Leu Gly Arg Leu Ser Gln Xaa Leu
1               5                   10                  15

His Arg Leu Gln Thr Xaa Pro Lys Thr Asp Val Gly Ala Asn Ala Pro
            20                  25                  30

<210> SEQ ID NO 66
<211> LENGTH: 32
<212> TYPE: PRT
<213> ORGANISM: Artificial Sequence
<220> FEATURE:
<223> OTHER INFORMATION: Synthetic Construct
<220> FEATURE:
<221> NAME/KEY: SITE
<222> LOCATION: 15
<223> OTHER INFORMATION: D or E
<220> FEATURE:
<221> NAME/KEY: SITE
<222> LOCATION: 22
<223> OTHER INFORMATION: F or Y

<400> SEQUENCE: 66

Cys Ala Ser Leu Ser Thr Cys Met Leu Gly Lys Leu Thr Gln Xaa Leu
1               5                   10                  15

His Lys Leu Gln Thr Xaa Pro Lys Thr Asp Val Gly Ala Asn Ala Pro
            20                  25                  30

<210> SEQ ID NO 67
<211> LENGTH: 32
<212> TYPE: PRT
<213> ORGANISM: Artificial Sequence
<220> FEATURE:
<223> OTHER INFORMATION: Synthetic Construct

<400> SEQUENCE: 67

Cys Ala Ser Leu Ser Thr Cys Val Leu Gly Arg Leu Ser Gln Glu Leu
1               5                   10                  15

His Arg Leu Gln Thr Phe Pro Lys Thr Asp Val Gly Ala Asn Ala Tyr
            20                  25                  30

<210> SEQ ID NO 68
<211> LENGTH: 32
<212> TYPE: PRT
<213> ORGANISM: Artificial Sequence
<220> FEATURE:
<223> OTHER INFORMATION: Synthetic Construct

<400> SEQUENCE: 68

Cys Ala Ser Leu Ser Thr Cys Met Leu Gly Lys Leu Thr Gln Glu Leu
1               5                   10                  15

His Lys Leu Gln Thr Phe Pro Lys Thr Asp Val Gly Ala Asn Ala Tyr
            20                  25                  30

<210> SEQ ID NO 69
<211> LENGTH: 32
<212> TYPE: PRT
<213> ORGANISM: Artificial Sequence
<220> FEATURE:
<223> OTHER INFORMATION: Synthetic Construct

<400> SEQUENCE: 69

Cys Ala Ser Leu Ser Thr Cys Val Leu Gly Lys Leu Ser Gln Asp Leu
1               5                   10                  15

His Lys Leu Gln Thr Phe Pro Lys Thr Asp Val Gly Ala Asn Ala Tyr
            20                  25                  30
```

<210> SEQ ID NO 70
<211> LENGTH: 32
<212> TYPE: PRT
<213> ORGANISM: Artificial Sequence
<220> FEATURE:
<223> OTHER INFORMATION: Synthetic Construct

<400> SEQUENCE: 70

Cys Ser Asn Leu Ser Thr Cys Met Leu Gly Arg Leu Ser Gln Glu Leu
1               5                   10                  15

His Arg Leu Gln Thr Phe Pro Lys Thr Asp Val Gly Ala Asn Ala Tyr
            20                  25                  30

<210> SEQ ID NO 71
<211> LENGTH: 32
<212> TYPE: PRT
<213> ORGANISM: Artificial Sequence
<220> FEATURE:
<223> OTHER INFORMATION: Synthetic Construct

<400> SEQUENCE: 71

Cys Ala Ser Leu Ser Thr Cys Val Leu Gly Arg Leu Ser Gln Glu Leu
1               5                   10                  15

His Arg Leu Gln Thr Phe Pro Arg Thr Asp Val Gly Ala Asn Ala Tyr
            20                  25                  30

<210> SEQ ID NO 72
<211> LENGTH: 32
<212> TYPE: PRT
<213> ORGANISM: Artificial Sequence
<220> FEATURE:
<223> OTHER INFORMATION: Synthetic Construct

<400> SEQUENCE: 72

Cys Ala Ser Leu Ser Thr Cys Met Leu Gly Lys Leu Thr Gln Glu Leu
1               5                   10                  15

His Lys Leu Gln Thr Phe Pro Arg Thr Asp Val Gly Ala Asn Ala Tyr
            20                  25                  30

<210> SEQ ID NO 73
<211> LENGTH: 32
<212> TYPE: PRT
<213> ORGANISM: Artificial Sequence
<220> FEATURE:
<223> OTHER INFORMATION: Synthetic Construct

<400> SEQUENCE: 73

Cys Ala Ser Leu Ser Thr Cys Val Leu Gly Arg Leu Ser Gln Glu Leu
1               5                   10                  15

His Arg Leu Gln Thr Phe Pro Lys Thr Asp Val Gly Ala Asn Ala Pro
            20                  25                  30

<210> SEQ ID NO 74
<211> LENGTH: 32
<212> TYPE: PRT
<213> ORGANISM: Artificial Sequence
<220> FEATURE:
<223> OTHER INFORMATION: Synthetic Construct

<400> SEQUENCE: 74

Cys Ala Ser Leu Ser Thr Cys Met Leu Gly Lys Leu Thr Gln Glu Leu
1               5                   10                  15

His Lys Leu Gln Thr Phe Pro Lys Thr Asp Val Gly Ala Asn Ala Pro
            20                  25                  30